United States Patent
Sengupta et al.

(10) Patent No.: US 9,512,428 B2
(45) Date of Patent: Dec. 6, 2016

(54) METHOD OF DERIVING MATURE HEPATOCYTES FROM HUMAN EMBRYONIC STEM CELLS

(71) Applicant: Wisconsin Alumni Research Foundation, Madison, WI (US)

(72) Inventors: Srikumar Sengupta, Madison, WI (US); James Thomson, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/822,099

(22) Filed: Aug. 10, 2015

(65) Prior Publication Data

US 2016/0032287 A1 Feb. 4, 2016

Related U.S. Application Data

(62) Division of application No. 13/772,802, filed on Feb. 21, 2013, now Pat. No. 9,127,253.

(60) Provisional application No. 61/706,327, filed on Sep. 27, 2012, provisional application No. 61/647,090, filed on May 15, 2012, provisional application No. 61/601,128, filed on Feb. 21, 2012.

(51) Int. Cl.

| | |
|---|---|
| *C12N 15/11* | (2006.01) |
| *C12N 15/113* | (2010.01) |
| *C12N 5/071* | (2010.01) |
| *A61K 35/407* | (2015.01) |
| *A61K 35/545* | (2015.01) |
| *G01N 33/50* | (2006.01) |
| *A61K 38/38* | (2006.01) |
| *A61K 38/44* | (2006.01) |
| *A61K 38/45* | (2006.01) |
| *A61K 38/57* | (2006.01) |

(52) U.S. Cl.
CPC ............ *C12N 15/113* (2013.01); *A61K 35/407* (2013.01); *A61K 35/545* (2013.01); *C12N 5/067* (2013.01); *C12N 5/0672* (2013.01); *C12N 15/111* (2013.01); *G01N 33/5014* (2013.01); *A61K 38/38* (2013.01); *A61K 38/44* (2013.01); *A61K 38/45* (2013.01); *A61K 38/57* (2013.01); *C12N 2310/141* (2013.01); *C12N 2320/30* (2013.01); *C12N 2501/65* (2013.01); *C12N 2510/00* (2013.01); *C12Y 114/13017* (2013.01); *C12Y 114/14001* (2013.01); *C12Y 206/01005* (2013.01)

(58) Field of Classification Search
CPC .............................. C12N 15/113; C12N 5/067
See application file for complete search history.

(56) References Cited

U.S. PATENT DOCUMENTS

| | | | |
|---|---|---|---|
| 6,506,574 B1 | 1/2003 | Rambhatla et al. | |
| 7,256,042 B2 | 8/2007 | Rambhatla et al. | |
| 7,282,366 B2 | 10/2007 | Rambhatla et al. | |
| 7,473,555 B2 | 1/2009 | Mandalam et al. | |
| 2005/0037493 A1 | 2/2005 | Mandalam et al. | |
| 2010/0086999 A1 | 4/2010 | Zhao et al. | |
| 2010/0143313 A1 | 6/2010 | Yarmush et al. | |
| 2011/0195056 A1 | 8/2011 | Pryor et al. | |

FOREIGN PATENT DOCUMENTS

| | | |
|---|---|---|
| EP | 2386627 A1 | 11/2011 |
| WO | 2010104796 A2 | 9/2010 |
| WO | 2010115050 A2 | 10/2010 |

OTHER PUBLICATIONS

Si-Tayeb et al. Hepatology 2010 51:297-305.*
Khetani et al. Nature Biotechnology 26:120-126, 2008.*
Cai, et al., Directed Differentiation of Human Embryonic Stem Cells Into Functional Hepatic Cells, Hepatology, 2007, 45:1229-1239.
Jung, et al., Epigenetic Modulation of miR-122 Facilitates Human Embryonic Stem Cell Self-Renewal and Hepatocellular Carcinoma Proliferation, PLoS ONE, 2011, 6(11):e27740, 14 pages.
Laudadio, et al., A Feedback Loop Between the Liver-Enriched Transcription Factor Network and Mir-122 Controls Hepatocyte Differentiation, Gastroenterology, 2012, 142:119-129.
Lewis, et al., Prediction of Mammalian MicroRNA Targets, Cell, 2003, 115:787-798.
Li, et al., Positive Regulation of Hepatic miR-122 Expression by HNF4a, Journal of Hepatology, 2011, 55(3):602-611.
Schwartz, et al., Modeling Hepatitis C Virus Infection Using Human Induced Pluripotent Stem Cells, PNAS, 2012, 109(7):2544-2548.
Takayama, et al., Efficient Generation of Functional Hepatocytes From Human Embryonic Stem Cells and Induced Pluripotent Stem Cells by HNF4a Transduction, Molecular Therapy, 2012, 20(1):127-137.

(Continued)

*Primary Examiner* — Brian Whiteman
(74) *Attorney, Agent, or Firm* — Quarles & Brady LLP

(57) ABSTRACT

A method for producing mature hepatocytes having functional hepatic enzyme activity from human pluripotent cells is disclosed. The method includes the step of transferring an external vector comprising the DNA sequence coding for a microRNA having the seed sequence of the microRNA miR-122, the DNA sequence coding for a microRNA having the seed sequence of the microRNA miR-let-7c, a microRNA having the seed sequence of the microRNA miR-122, a microRNA having the seed sequence of the microRNA miR-let-7c, or a combination thereof into one or more fetal hepatocytes. The resulting cells differentiate into mature hepatocytes that exhibit functional hepatic enzyme activity, and can be used in drug metabolism and toxicity testing, in the study of viruses that target hepatic tissue, and as therapeutics.

A related method of maintaining the functional hepatic enzyme activity of primary hepatocytes over time is also disclosed. The method includes the step of transferring an external vector comprising the DNA sequence coding for a microRNA having the seed sequence of the microRNA miR-122 into one or more cultured primary hepatocytes.

3 Claims, 23 Drawing Sheets

(56) References Cited

OTHER PUBLICATIONS

Xu, et al., Liver-Enriched Transcription Factors Regulate MicroRNA-122 That Targets CUTL1 During Liver Development, Hepatology, 2010, 52:1431-1442.
PCT International Search Report and Written Opinion, PCT/US2013/027124, May 17, 2013, 11 pages.
Chang et al. RNA Biology 1:2, 106-113, 2004.
Tzur et al. Plos One 3: e3726, pp. 1-15, 2008.
Kim et al. Heptalogy Research 2011: 41: 170-183.
Doddapaneni et al. J. of Cellular Biochemistry 114: 1575-1583, 2013.
Girard et al. J. of Hepatology 48, 2008, 648-656.
Bolleyn, Jennifer, et al. "Effect of Trichostatin A on miRNA expression in cultures of primary rat hepatocytes" Toxicology In Vitro 25.6 (Sep. 2011): 1173-1182. Epub Apr. 13, 2011.
Michalopoulos, George, et al. "Cytochrome P-450 induction by phenobarbital and 3-methylcholanthrene in primary cultures of hepatocytes." Science 193.4256 (Sep. 1976): 907-909.
Michalopoulos, G., and H. C. Pitot. "Primary culture of parenchymal liver cells on collagen membranes: morphological and biochemical observations." Experimental cell research 94.1 (Aug. 1975): 70-78.
Savage, C. Richard, and Robert J. Bonney. "Extended expression of differentiated function in primary cultures of adult liver parenchymal cells maintained on nitrocellulose filters: I. Induction of phosphoenolpyruvate carboxykinase and tyrosine aminotransferase." Experimental cell research 114.2 (Jul. 1978): 307-315.
Vinken, Mathieu, Tamara Vanhaecke, and Vera Rogiers. "Primary hepatocyte cultures as in vitro tools for toxicity testing: quo vadis?." Toxicology in Vitro 26.3 (Apr. 2012): 541-544.

\* cited by examiner

SEQUENCE LISTING

<160> NUMBER OF SEQ ID NOS: 22

<210> SEQ ID NO 1
<211> LENGTH: 85
<212> TYPE: RNA
<213> ORGANISM: Homo sapiens

<400> SEQUENCE: 1
ccuuagcaga gcuguggagu gugacaaugg uguuuguguc uaaacuauca aacgccauua      60
ucacacuaaa uagcuacugc uaggc                                           85

<210> SEQ ID NO 2
<211> LENGTH: 22
<212> TYPE: RNA
<213> ORGANISM: Homo sapiens

```
<400> SEQUENCE: 2
uggagvguga caaugguguu ug                                                22

<210> SEQ ID NO 3
<211> LENGTH: 84
<212> TYPE: RNA
<213> ORGANISM: Homo sapiens

<400> SEQUENCE: 3
gcauccgggu ugagguagua gguuguaugg uuuagaguua cacccuggga guuaacugua        60
caaccuucua gcuuuccuug gagc                                              84

<210> SEQ ID NO 4
<211> LENGTH: 22
<212> TYPE: RNA
<213> ORGANISM: Homo sapiens

<400> SEQUENCE: 4
ugagguagua gguuguaugg uu                                                22

<210> SEQ ID NO 5
<211> LENGTH: 10
<212> TYPE: RNA
<213> ORGANISM: Homo sapiens

<400> SEQUENCE: 5
uggaguguga                                                              10

<210> SEQ ID NO 6
<211> LENGTH: 10
<212> TYPE: RNA
<213> ORGANISM: Homo sapiens

<400> SEQUENCE: 6
ugagguagua                                                              10

<210> SEQ ID NO 7
<211> LENGTH: 10
<212> TYPE: RNA
<213> ORGANISM: Homo sapiens

<400> SEQUENCE: 7
agagguagua                                                              10

<210> SEQ ID NO 8
<211> LENGTH: 10
<212> TYPE: RNA
<213> ORGANISM: Homo sapiens

<400> SEQUENCE: 8
ugagguagga                                                              10

<210> SEQ ID NO 9
<211> LENGTH: 22
<212> TYPE: DNA
<213> ORGANISM: Artificial Sequence
<220> FEATURE:
<223> OTHER INFORMATION: GAPDH forward QPCR primer

<400> SEQUENCE: 9
tcaacgacca ctttgtcaag ct                                                22
```

```
<210> SEQ ID NO 10
<211> LENGTH: 19
<212> TYPE: DNA
<213> ORGANISM: Artificial Sequence
<220> FEATURE:
<223> OTHER INFORMATION: GAPDH reverse QPCR primer

<400> SEQUENCE: 10
ccatgaggtc caccaccct                                              19

<210> SEQ ID NO 11
<211> LENGTH: 25
<212> TYPE: DNA
<213> ORGANISM: Artificial Sequence
<220> FEATURE:
<223> OTHER INFORMATION: ALB forward QPCR primer

<400> SEQUENCE: 11
caaagatgtg ttgctatcct gaaaa                                       25

<210> SEQ ID NO 12
<211> LENGTH: 25
<212> TYPE: DNA
<213> ORGANISM: Artificial Sequence
<220> FEATURE:
<223> OTHER INFORMATION: ALB reverse QPCR primer

<400> SEQUENCE: 12
ccgaagtgga ataagagaga acact                                       25

<210> SEQ ID NO 13
<211> LENGTH: 22
<212> TYPE: DNA
<213> ORGANISM: Artificial Sequence
<220> FEATURE:
<223> OTHER INFORMATION: AFP forward QPCR primer

<400> SEQUENCE: 13
cttgaggctg tcattgcaga tt                                          22

<210> SEQ ID NO 14
<211> LENGTH: 17
<212> TYPE: DNA
<213> ORGANISM: Artificial Sequence
<220> FEATURE:
<223> OTHER INFORMATION: AFR reverse QPCR primer

<400> SEQUENCE: 14
cctggccttg gcagcat                                                17

<210> SEQ ID NO 15
<211> LENGTH: 17
<212> TYPE: DNA
<213> ORGANISM: Artificial Sequence
<220> FEATURE:
<223> OTHER INFORMATION: CYP1A2 forward QPCR primer

<400> SEQUENCE: 15
gcccggccca caattaa                                                17

<210> SEQ ID NO 16
<211> LENGTH: 20
<212> TYPE: DNA
<213> ORGANISM: Artificial Sequence
<220> FEATURE:
<223> OTHER INFORMATION: CYP1A2 reverse QPCR primer
```

```
<400> SEQUENCE: 16
gctaatgggt gcagggtttc                                              20

<210> SEQ ID NO 17
<211> LENGTH: 22
<212> TYPE: DNA
<213> ORGANISM: Artificial Sequence
<220> FEATURE:
<223> OTHER INFORMATION: CYP3A4 forward QPCR primer

<400> SEQUENCE: 17
ggcaggagaa tcacttgaac ct                                           22

<210> SEQ ID NO 18
<211> LENGTH: 21
<212> TYPE: DNA
<213> ORGANISM: Artificial Sequence
<220> FEATURE:
<223> OTHER INFORMATION: CYP3A4 reverse QPCR primer

<400> SEQUENCE: 18
gagtgcagtg gtgcaatctc a                                            21

<210> SEQ ID NO 19
<211> LENGTH: 25
<212> TYPE: DNA
<213> ORGANISM: Artificial Sequence
<220> FEATURE:
<223> OTHER INFORMATION: CYP7A1 forward QPCR primer

<400> SEQUENCE: 19
ggagtgtatt aagtgcagct tgaca                                        25

<210> SEQ ID NO 20
<211> LENGTH: 24
<212> TYPE: DNA
<213> ORGANISM: Artificial Sequence
<220> FEATURE:
<223> OTHER INFORMATION: CYP7A1 reverse QPCR primer

<400> SEQUENCE: 20
caccttagtt ttttcatct gcaa                                          24

<210> SEQ ID NO 21
<211> LENGTH: 19
<212> TYPE: DNA
<213> ORGANISM: Artificial Sequence
<220> FEATURE:
<223> OTHER INFORMATION: HBV forward QPCR primer

<400> SEQUENCE: 21
cctatgggag tgggcctca                                               19

<210> SEQ ID NO 22
<211> LENGTH: 24
<212> TYPE: DNA
<213> ORGANISM: Artificial Sequence
<220> FEATURE:
<223> OTHER INFORMATION: HBV reverse QPCR primer

<400> SEQUENCE: 22
ccccaatacc acatcatcca tata                                         24
```

METHOD OF DERIVING MATURE HEPATOCYTES FROM HUMAN EMBRYONIC STEM CELLS

CROSS-REFERENCE TO RELATED APPLICATIONS

This application is a divisional of U.S. application Ser. No. 13/772,802 filed on Feb. 21, 2013, which claims the benefit of U.S. Provisional Application Nos. 61/601,128 filed on Feb. 21, 2012, 61/647,090 filed on May 15, 2012, and 61/706,327 filed on Sep. 27, 2012. Each of these applications is incorporated by reference herein in its entirety.

STATEMENT REGARDING FEDERALLY SPONSORED RESEARCH OR DEVELOPMENT

This invention was made with government support under ES017166 awarded by the National Institutes of Health. The government has certain rights in the invention.

BACKGROUND

The human liver is the primary site for detoxification of ingested chemicals and also facilitates the metabolic breakdown of a wide range of pharmaceutical compounds. Primary hepatocytes, isolated from liver tissue and subsequently cultured, can be used to test the metabolic breakdown and toxicity of various compounds. However, primary hepatocytes do not divide, and when cultured, rapidly lose their ability to produce functional hepatic enzymes. In addition, inherent variability between different preparations of primary hepatocytes complicates comparisons of results obtained from different primary hepatocyte cultures.

Although it has been suggested that human embryonic stem cells (hESCs) or induced pluripotent stem cells (iPSCs) could be differentiated to mature hepatocytes suitable for these purposes, cells isolated to date from these pluripotent cells are fetal, or immature, in nature, notwithstanding their hepatocyte-like morphology. As a result, they produce functional hepatic enzymes needed for testing purposes in very small quantities, if at all.

Accordingly, it is recognized in the art that the term "hepatocyte" should not be broadly applied to include stem cell-derived fetal hepatocytes that express some markers expressed by primary hepatocytes, unless the cells also produce functional hepatic enzymes in quantities comparable to the quantities produced by primary hepatocytes. For example, Hengstler et al. (Expert Opin. Drug Metab. Toxicol. (2005) 1(1): 61-74) state that the term "hepatocyte" should only be used to define stem cell-derived cells that both express known hepatocyte markers and produce quantities of functional hepatic enzymes that are comparable to the quantities produced by primary hepatocytes (page 63). Furthermore Hengstler et al. explain that a "hepatocyte" should exhibit drug metabolism capabilities and should be capable of generating toxic metabolites as human primary hepatocytes would (page 62, col. 2). Finally, Hengstler et al. indicate that qualitative assays like reverse transcription PCR and immunochemical staining are not sufficient to establish that cells are hepatocytes, and that quantitative assays that include human hepatocyte controls are required to demonstrate the generation of true hepatocytes (page 63, col. 2; page 71). As another example, Soto-Gutierrez et al. (Biotechnology and Genetic Engineering Reviews (2008) 25: 149-164) emphasize that a "hepatocyte" should be defined to encompass only cells that are able to perform the functions of primary hepatocytes, including metabolizing xenobiotics or other endogenous substances (page 155).

Cai et al. previously reported the differentiation of human embryonic stem cells into hepatic cells (Hepatology (2007) 45: 1229-1239). Although Cai et al. purportedly show the expression of some functional genes, they presented no confirmatory quantitative or drug metabolism data. The expression of functional genes was demonstrated by reverse transcription PCR and immunochemical staining, neither of which is quantitative. In these assays, minute quantities of RNA and protein, respectively, can result in a positive test, and there is no accurate indication of the quantity of gene expression occurring in the cell. Furthermore, no comparison is made to results obtained using human hepatocyte controls. As discussed above, these results are insufficient to establish the formation of true hepatocytes.

When the inventors used a protocol similar to that described by Cai et al., they obtained cells having hepatocyte morphology and expressing some genes characteristic of hepatocytes. However, when such gene expression was quantitatively measured and compared to that of primary human hepatocytes isolated from liver tissue, the expression levels were found to be too low to label the resulting cells as true hepatocytes. Thus, these cells are more properly considered fetal hepatocytes, not true hepatocytes.

Takayama et al. recently reported the production of functional hepatocytes from human embryonic stem cells and human induced pluripotent stem cells using a protocol similar to that used by Cai et al., but additionally including the sequential transduction of three separate factors: SOX17, HEX, and HNF4α (Molecular Therapy (8 Nov. 2011); doi:10.1038/mt. 2011.234: 1-11). Because the Takayama protocol requires three separate transductions, it would be too complex and time consuming to readily put into practice on a larger scale. Furthermore, improved enzyme induction with known inducing agents and higher levels of CYP enzyme expression than is reported by Takayama et al. would be desired in hepatocytes used for metabolism or toxicity testing.

Thus, there is a need in the art for an improved, relatively simple, replicable and standardized method of producing mature hepatocyte cultures that have the ability to produce functional hepatic enzymes for an extended period of time, for use in toxicity and metabolism testing.

BRIEF SUMMARY

This disclosure relates generally to new methods of using microRNAs having the functionality of mir-122, microRNAs having the functionality of let-7c, or external vectors containing the DNA sequence coding for such microRNAs.

In a first aspect, the disclosure encompasses a method for producing mature hepatocytes having functional hepatic enzyme activity from human pluripotent cells. The method includes the step of transferring (a) a microRNA comprising a core sequence that is 18 to 24 nucleotides long, wherein the 10 nucleotide sequence on the 5' end of the core sequence comprises a seed sequence that contains at least six consecutive nucleotides of the ten-nucleotide 5' end of the microRNA miR-122 (SEQ ID NO:5), or an external vector containing the DNA coding sequence for such a microRNA; (b) a microRNA comprising a core sequence that is 18 to 24 nucleotides long, wherein the 10 nucleotide sequence on the 5' end of the core sequence comprises a seed sequence that contains at least six consecutive nucleotides of the ten nucleotide 5' end of any of the let-7 microRNA family (SEQ ID NO:6, SEQ ID NO:7, or SEQ ID NO:8), or an external vector containing the DNA coding sequence for such a microRNA; or both (a) and (b) into one or more fetal hepatocytes obtained from human pluripotent cells. The cells then differentiate further into mature hepatocytes exhibiting functional hepatic enzyme activity. Examples of human pluripotent cells from which the fetal hepatocytes can be obtained include human induced pluripotent stem cells and human embryonic stem cells.

In embodiments where the microRNA itself is transferred, it may be transferred as single or double stranded microRNA, with or without chemically modified ends. In some embodiments, the microRNA seed sequence from miR-122 consists of the sequence of nucleotides 2-8 of SEQ ID NO:5. In some such embodiments, the microRNA may include the complete sequence of either miR-122 (SEQ ID NO:2) or mir-122 (SEQ ID NO:1).

In some embodiments, the microRNA seed sequence from the let-7 microRNA family consists of nucleotides 1-8 of SEQ ID NO:6. In such embodiments, the microRNA may include the complete sequence of either miR-let-7c (SEQ ID NO:4) or let-7c (SEQ ID NO:3).

In some embodiments, the step of transferring the external vector or the microRNA into the fetal hepatocytes may be performed by transduction or transfection. The vector may be configured such that after transfer, the DNA sequence coding for the microRNA is integrated into the chromosomal DNA of the fetal hepatocytes, or the vector may be configured such that after transfer, the DNA sequence coding for the microRNA exists episomally within the fetal hepatocytes.

The type of vector used in the method is not limited. In some embodiments, the vector is a viral vector and the transfer is by transduction. Non-limiting examples of such a vector include a lentiviral vector, such as pEZX-MR01 or pEZX-MR03. In other embodiments, transfer of the vector or of the microRNA occurs by non-viral transfection. Non-viral transfection can be facilitated by a number of techniques, including without limitation electroporation or the use of chemical transfection agents known in the art. In certain such embodiments, the external vector comprises a transposon, such as a PiggyBac transposon. Optionally, the vector may be configured for insertion into the Rosa26 locus of the fetal hepatocytes.

In some embodiments where either the microRNA that includes a seed sequence from miR-122 or an external vector comprising the DNA sequence coding for such a microRNA is transferred into the fetal hepatocytes, the resulting mature hepatocytes express one or more of the liver proteins albumin, alpha-1-antitrypsin (AAT), tyrosine aminotransferase (TAT), CYP1A2, CYP7A1 or CYP3A4 at a level that is at least 70% of the expression level of these liver proteins in fresh primary hepatocytes. In some such embodiments, the mature hepatocytes express CYP3A4 at a level that is at least 70% of the expression level in fresh primary hepatocytes. In other such embodiments, the mature hepatocytes express CYP1A2 at a level that is at least 1.5 times greater than the expression level in fresh primary hepatocytes. In another such embodiment, the mature hepatocytes express at least 5-fold more CYP7A1 than fresh primary hepatocytes.

In some embodiments where either the microRNA that includes a seed sequence from one or more of the miR-let-7 family or an external vector comprising the DNA sequence coding for such a microRNA is transferred into the fetal hepatocytes, the resulting mature hepatocytes express one or more of the liver proteins albumin, CYP1A2, CYP7A1 or CYP3A4 at a level that is greater than the expression level of these liver proteins in fresh primary hepatocytes. In some such embodiments, the mature hepatocytes express albumin, CYP1A2, CYP7A1 or CYP3A4 at a level that is at least 5 times greater than the expression level in fresh primary hepatocytes. In other such embodiments, the mature hepatocytes express all of these proteins at a level that is at least 5 times greater than the expression level in fresh primary hepatocytes. In still other such embodiments, the microRNA that contains a seed sequence of the microRNA mir-122 or an external vector comprising the DNA sequence coding for such a microRNA is also transferred into the fetal hepatocytes. In some such embodiments, the mature hepatocytes express the fetal marker alpha-feto protein (AFP) at a level that is less than 20% of the expression level in fetal hepatocytes initially obtained from human pluripotent cells.

In some embodiments, the mature hepatocytes are shown to metabolize one or more drugs, using a standard in vitro metabolism assay. Examples of drugs that can be used in such assays are omeprazole and rifampicin. In certain embodiments, mature hepatocytes treated with omeprazole show increased levels of CYP1A2 enzyme, or mature hepatocytes treated with rifampicin show increased levels of CYP3A4 enzyme.

In a second aspect, the disclosure encompasses the mature hepatocytes having functional hepatic enzyme activity that are produced by the method summarized above. The mature hepatocytes may have a far greater number of miR-122 RNA molecules, miR-let-7c molecules, or both present within the cell than are present in fetal hepatocytes. In certain embodiments, the number of miR-122 RNA molecules, miR-let-7c molecules, or both present within the cell is at least 50% greater than the number of such molecules present in fetal hepatocytes.

In a third aspect, the disclosure encompasses a method for testing the potential toxicity of a compound. In one embodiment, such a method includes the steps of (a) exposing one or more mature hepatocytes produced by the method described above to the compound, and (b) monitoring the one or more mature hepatocytes for signs of toxicity. In another embodiment, such a method includes the steps of (a) exposing one or more mature hepatocytes produced by the method described above to the compound, wherein the compound is metabolized by the hepatocytes; (b) contacting the resulting metabolite(s) of the compound with one or more non-hepatocyte cells; and (c) monitoring the non-hepatocyte cells for any metabolite-induced changes. Non-limiting examples of non-hepatocyte cells that could be used in the method include neurons or cardiomyocytes.

In a fourth aspect, the disclosure encompasses a method for studying the metabolism of a compound. Such a method includes the steps of (a) exposing one or more mature hepatocytes produced by the method described above to the compound; and (b) determining what metabolites are produced by the hepatic processing of the compound.

In a fifth aspect, the disclosure encompasses a method of treating a liver disorder. In one embodiment, such a method includes the step of administering one or more mature hepatocytes produced by the method described above to a patient having a liver disorder. Non-limiting examples of liver disorders that could be treated using this method include acute liver damage or a metabolic liver disease, such as alpha 1 antitrypsin deficiency or Wilson's disease.

In another embodiment, liver inflammation caused by a viral infection can be treated by administering to a patient having liver inflammation caused by a viral infection an effective amount of (a) a microRNA comprising a core sequence that is 18 to 24 nucleotides long, wherein the 10 nucleotide sequence on the 5' end of the core sequence comprises a seed sequence that contains at least six consecutive nucleotides of the ten nucleotide 5' end of any of the let-7 microRNA family (SEQ ID NO:6, SEQ ID NO:7, or SEQ ID NO:8), or both such a microRNA and a second microRNA that comprises a core sequence that is 18 to 24 nucleotides long, wherein the 10 nucleotide sequence on the 5' end of the core sequence comprises a seed sequence that contains at least six consecutive nucleotides of the ten-nucleotide 5' end of the microRNA miR-122 (SEQ ID NO:5); (b) one or more cells comprising the microRNA or microRNA combination of (a); or (c) an agent that upregulates the expression of the microRNA let-7c or the expression of both the microRNA let-7c and the microRNA mir-122. Such treatment would reduce the viral load of the liver, resulting in decreased liver inflammation.

In certain embodiments where the microRNA contains a seed sequence from the let-7 microRNA family, the seed sequence consists of nucleotides 1-8 of SEQ ID NO:6. In some such embodiments, the microRNA includes the complete sequence of let-7c (SEQ ID NO:3) or miR-let-7c (SEQ ID NO:4).

In certain embodiments where the second microRNA contains a seed sequence from miR-122, the seed sequence consists of nucleotides 2-8 of SEQ ID NO:5. In some such embodiments, the second microRNA includes the complete sequence of mir-122 (SEQ ID NO:1) or miR-122 (SEQ ID NO:2).

In embodiments where liver inflammation caused by viral infection is treated, the viral infection may be a hepatitis virus infection, including without limitation HBV or HCV. Reduced liver inflammation accomplished by using the method would result in reduced incidence and severity of disorders caused by liver inflammation, including without limitation fibrosis of the liver, cirrhosis of the liver, and liver cancer.

In a sixth aspect, the disclosure encompasses a method for maintaining the functional hepatic enzyme activity of primary hepatocytes. Such a method includes the step of transferring a microRNA comprising a core sequence that is 18 to 24 nucleotides long, wherein the 10 nucleotide sequence on the 5' end of the core sequence comprises a seed sequence that contains at least six consecutive nucleotides of the ten-nucleotide 5' end of the microRNA miR-122 (SEQ ID NO:5), or an external vector containing the DNA coding sequence for such a microRNA, into one or more cultured primary hepatocytes. The primary hepatocytes produced by this method maintain higher levels of functional hepatic enzyme activity after several days of culture than do control primary hepatocytes. In some embodiments, the seed sequence of the microRNA consists of nucleotides 2-8 of SEQ ID NO:5. In such embodiments, the microRNA may include the complete sequence of mir-122 (SEQ ID NO:1) or miR-122 (SEQ ID NO:2).

In some embodiments, the external vector or the microRNA is transferred by transduction or transfection. The vector may be configured such that after transfer, the DNA sequence coding for the microRNA is integrated into the chromosomal DNA of the hepatocytes, or the vector may be configured such that after transfer, the DNA sequence coding for the microRNA exists episomally within the hepatocytes.

The type of vector used in the method is not limited. In some embodiments, the vector is a viral vector and the transfer is by transduction. Non-limiting examples of such a vector include a lentiviral vector, such as pEZX-MR01. In other embodiments, transfer of the vector or the microRNA is by non-viral transfection. Non-viral transfection can be facilitated by a number of techniques, including without limitation electroporation or the use of chemical transfection agents known in the art. In certain such embodiments, the external vector comprises a transposon, such as a PiggyBac transposon. Optionally, the vector may be configured for insertion into the Rosa26 locus of the hepatocytes.

In some embodiments, after thirteen days of culture, the mir-122 expressing primary hepatocytes express at least 2.5-fold more cytochrome CYP1A2 enzyme and 50-fold more cytochrome 7A1 enzyme than is expressed in 13 day old primary control hepatocytes. In some embodiments, after 19 days of culture, the mir-122 expressing primary hepatocytes express at least 2-fold more cytochrome 3A4 enzyme than is expressed in primary control hepatocytes that are 19 days old.

In a seventh aspect, the disclosure encompasses an in vitro method for supporting the replication of hepatitis virus. The method includes the step of exposing one or more mature hepatocytes prepared according to the methods described herein to a hepatitis virus. The hepatitis virus replicates within the one or more mature hepatocytes. In certain embodiments, the hepatitis virus is hepatitis B virus (HBV) or hepatitis C virus (HCV).

In an eighth aspect, the disclosure encompasses a cell culture comprising one or more isolated hepatocytes having certain defining characteristics that can be measured after several days of culture. Specifically, in one embodiment, after nine days of culture, at least one of the hepatocytes maintains an expression level for tyrosine aminotransferase (TAT) that is at least 80% of the level that was exhibited when the culture was established. In this or other embodiments, after 13 days of culture, the hepatocytes maintain (a) expression levels of CYP1A2 and CYP7A1 that are at least equal to, and preferably at least 2-fold more, than the expression levels that were exhibited when the culture was established. In these or other embodiments the expression level of CYP3A4 after 19 days of culture that is greater than when the culture was established.

In a ninth aspect, the disclosure encompasses a method of treating hepatocellular carcinoma. The method includes the step of administering to a patient having a hepatocellular carcinoma an effective amount of (a) a microRNA comprising a core sequence that is 18 to 24 nucleotides long, wherein the 10 nucleotide sequence on the 5' end of the core sequence comprises a seed sequence that contains at least six consecutive nucleotides of the ten-nucleotide 5' end of the microRNA miR-122 (SEQ ID NO:5); a microRNA comprising a core sequence that is 18 to 24 nucleotides long, wherein the 10 nucleotide sequence on the 5' end of the core sequence comprises a seed sequence that contains at least six consecutive nucleotides of the ten nucleotide 5' end of any of the let-7 microRNA family (SEQ ID NO:6, SEQ ID NO:7, or SEQ ID NO:8); or both; or (b) an agent that upregulates the expression of the microRNA mir-122, the expression of the microRNA let-7c, or the expression of both the microRNA let-7c and the microRNA mir-122.

In some embodiments where the microRNA contains a seed sequence from the microRNA miR-122, the seed sequence consists of nucleotides 2-8 of SEQ ID NO:5. In some such embodiments, the microRNA may include the complete sequence of mir-122 (SEQ ID NO:1) or miR-122 (SEQ ID NO:2).

In some embodiments where the microRNA contains a seed sequence from the let-7 family, the seed sequence consists of nucleotides 1-8 of SEQ ID NO:6. In some such embodiments, the microRNA may include the complete sequence of let-7c (SEQ ID NO:3) or miR-let-7c (SEQ ID NO:4).

The methods and cell cultures of the invention are further detailed below.

BRIEF DESCRIPTION OF THE DRAWINGS

The disclosure will be better understood and features, aspects and advantages other than those set forth above will become apparent when consideration is given to the following detailed description thereof. Such detailed description makes reference to the following drawings.

Figure 1A:
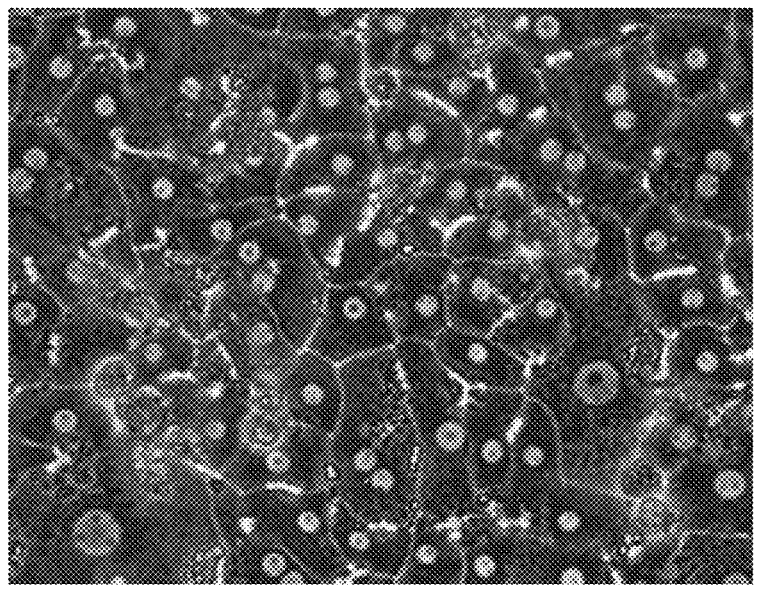
FIGS. 1A and 1B are photomicrographs of primary hepatocytes derived from human liver (FIG. 1A) and fetal hepatocytes derived from human embryonic stem cells (FIG. 1B). The photograph in FIG. 1B was taken before cells were transduced by mir-122. The two groups of cells are morphologically similar; however, the cells of FIG. 1B did not exhibit functional hepatic enzyme activity.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION

This disclosure relates generally to new methods of using microRNAs having the functionality of mir-122, microRNAs having the functionality of let-7c, or external vectors containing the DNA sequence coding for such microRNAs.

As is well-known in the art, a microRNA (miRNA) is a short ribonucleic acid molecule produced by eukaryotic cells. MiRNAs have three forms. The first form is designated the "pri-miRNA," and is the primary transcript that is transcribed directly from the genome. The pri-miRNA contains a sequence that can fold onto itself, forming a stem-loop structure. This stem-loop sequence of the pri-miRNA is excised in the nucleus by Drosha, a Class 2 RNAse III enzyme. The resulting excised RNA is designated as the "pre-miRNA." The pre-miRNA is then exported from the nucleus into the cytoplasm, where it is further processed by Dicer, a Class 3 RNAse III enzyme, forming the mature miRNA. The mature miRNA has a double stranded structure that is 18-24 nucleotides in length.

Names are assigned to experimentally-confirmed miRNAs before publication of their discovery. The prefix "mir" is followed by a dash and a number. The uncapitalized "mir-" refers to the pre-miRNA, while the capitalized "miR-" refers to the fully processed mature form. The DNA coding for the pre-miRNA is designated by the italicized mir-. In the case of the so-called lethal-7 (let-7) gene family miRNAs, the "mir" prefix is often omitted, and the name may include the prefix "let" followed by a dash and a 7(letter). Let-7c is a specific member of the mir-let-7 family of miRNAs. The pre-miRNA is designated "let-7c," and the DNA coding for the pre-miRNA is designated by the italicized "let-7c." The mature miRNA is designated "miR-let-7c."

The DNA coding for a miRNA has the same nucleotide sequence as the miRNA that it is coding for, except that the DNA coding sequence has a thymine (T) wherever the miRNA sequence has a uracil (U). In the Examples below, the DNA that codes for the pre-miRNA (i.e., "mir-122" or "let-7c") was transferred with the rest of the vector into the target cell.

The species of origin for a miRNA is designated with a three-letter prefix. For example, "hsa-miR-122" is a human miR-122. In this disclosure "mir-122," "miR-122" and "mir-122" refer to the human forms of the pre-miRNA, the mature miRNA, and the encoding DNA of mir-122, respectively. The nucleotide sequence for hsa-mir-122 (mir-122, the pre-miRNA) is CCUUAGCAGAGCUGUGGAGUGUGACAAUGGUGUUUGUGUCUAAACUA UCAAACGCCAUUAUCACACUAAAUAGCUACUGCUAGGC (SEQ ID NO:1). The nucleotide sequence for hsa-miR-122 (miR-122, the mature miRNA) is 5' UGGAGUGUGACA AUGGUGUUUG 3' (SEQ ID NO:2).

In this disclosure "let-7c," miR-let-7c, and "let-7c" refer to the human forms of the pre-miRNA, the mature miRNA, and the encoding DNA of let-7c, respectively (i.e., hsa-let-7c, hsa-miR-let-7c, and hsa-let-7c). The sequence for hsa-let-7c (let-7c, the pre-miRNA) is GCAUCCGGGUUGAGGUAGUAGGUUGUAUGGUUUAGAGUUACACCCUG GGAGUUA ACUGUACAACCUUCUAGCUUUCCUUG-GAGC (SEQ ID NO:3). The nucleotide sequence for hsa-miR-let-7c (miR-let-7c, the mature miRNA) is 5' UGAGGUAGUAGGUUGUAUGGUU 3' (SEQ ID NO:4).

There are two structural characteristics of a mature miRNA that are necessary and sufficient to carry out its function. The first characteristic is that the mature miRNA is 18-24 nucleotides long. Once Dicer processes the miRNA into its mature form, the guide strand gets incorporated into the RNA-induced silencing complex (RISC), a multiprotein complex that facilitates the recognition of the miRNA target site. The 18-24 nucleotide length of mature miRNAs is likely essential for incorporating the miRNAs into RISC. Accordingly, synthetic short interfering RNAs (siRNAs), which also act via RISC, are generally designed to be between 19 and 21 nucleotides long.

The second characteristic essential for the mature miRNA to carry out its function is the presence of a specific "seed" sequence at the 5' end. The seed sequence is generally a 6-8 nucleotide sequence within the 10-nucleotide sequence at the 5' end of a mature miRNA. Although it may occur anywhere within the 10-nucleotide sequence at the 5' end, the seed sequence generally starts at either at position 1 or position 2, relative to the 5' end of the mature miRNA. The specific seed sequence for a given miRNA may vary somewhat, depending on the complementary sequence present on its target gene. The presence of the seed sequence within the 10-nucleotide sequence at the 5' end of a mature miRNA is both necessary and sufficient for the bioactivity of the miRNA (See, Lewis, et al., Cell (2003) 115:787-798; Brennecke, et al., PLoS Biol (2005) 3(3): e85, 0404-0418). If the seed sequence is present, bioactivity can be maintained even if the sequence of the rest of the miRNA is varied.

This disclosure is related to the use or expression of two different specific miRNAs: miR-122 and miR-let-7c. The disclosed methods related to miR-122 would work with any microRNA having the functionality of mir-122 or an external vector containing the DNA sequence coding for such a microRNA (e.g., mir-122). In order to "have the functionality" of miR-122, the microRNA must have a core sequence that is 18-24 nucleotides long. This core sequence is what will form the mature miRNA. In addition, the core sequence must contain, within its 10-nucleotide 5' end, a specific miRNA seed sequence.

The seed sequence for miR-122 was determined using the TargetScan software (Massachusetts Institute of Technology), based on conservation of the miRNA's complementary sequence on its target gene across multiple species. For miR-122, the preferred seed sequence includes nucleotides 2-8 of the 10-nucleotide 5' end of miR-122 (UGGAGU-GUGA; SEQ ID NO:5). However, it is recognized in the art that the seed sequence may vary, while still maintaining miRNA function. Accordingly, a microRNA having a 18-24 nucleotide core sequence that includes a seed sequence within the 10-nucleotides on the 5' end of the core that consists of any 6, 7, 8, 9 or 10 consecutive nucleotides of the 10-nucleotide 5' end of the miR-122 sequence (SEQ ID NO:5) would have the same function as miR-122.

Thus, in addition to the preferred seed sequence (nucleotides 2-8 of SEQ ID NO:5), other sequences that could make up the seed sequence of a miRNA having the functionality of miR-122 include nucleotides 1-10, 1-9, 2-10, 2-9, 3-10, 1-7, 2-8, 3-9, 4-10, 1-6, 2-7, 3-8, 4-9, and 5-10 of SEQ ID NO:5.

The methods related to miR-let-7c would work with any microRNA having the functionality of miR-let-7c or an external vector containing the DNA sequence coding for such a microRNA (e.g., let-7c). In order to "have the functionality" of miR-let-7c, the microRNA must have a core sequence that is 18-24 nucleotides long. This core sequence is what will form the mature miRNA. In addition, the core sequence must contain, within its 10-nucleotide 5' end, a specific miRNA seed sequence.

The seed sequence for miR-let-7c was determined using the TargetScan software (Massachusetts Institute of Technology), based on conservation of the miRNA's complementary sequence on its target gene across multiple species. For miR-let-7c, the preferred seed sequence includes nucleotides 1-8 of the 10-nucleotide 5' end of miR-let-7c (UGAGGUAGUA; SEQ ID NO:6). However, it is recognized in the art that the seed sequence may vary, while still maintaining miRNA function. Accordingly, a microRNA having a 18-24 nucleotide core sequence that includes a seed sequence within the 10-nucleotides on the 5' end of the core that consists of any 6, 7, 8, 9 or 10 consecutive nucleotides of the 10-nucleotide 5' end of the miR-let-7c (SEQ ID NO:6, which is the same as the sequence at the 10-nucleotide 5' end of miR-let-7a, miR-let-7b, miR-let-7f, miR-let-7g, and miR-let-7i) would have the same functionality as miR-let-7c.

Furthermore, other members of the let-7 family (7a-7i) have similar or identical seed sequences, and would be expected to have the functionality of miR-let-7c. The 10-nucleotide 5' ends of miR-let-7d and miR-let-7e vary in a single nucleotide from the same region of the other let-7 family members. Specifically, the first nucleotide of miR-let-7d is A instead of U, and the ninth nucleotide of miR-let-7e is G instead of U. Because all members of this family have similar functionality, and because the variations from the preferred sequence are minor, a microRNA having a 18-24 nucleotide core sequence that includes a seed sequence within the 10-nucleotides on the 5' end of core that consists of any 6, 7, 8, 9 or 10 consecutive nucleotides of the 10-nucleotide 5' ends of the miR-let-7d (AGAGGUAGUA; SEQ ID NO:7) or miR-let-7e (UGAGGUAGGA; SEQ ID NO:8) would also be expected to have the same functionality as miR-let-7c.

Thus, in addition to the preferred seed sequence (nucleotides 1-8 of SEQ ID NO:6), other sequences that could make up the seed sequence of a miRNA having the functionality of miR-let-7c include nucleotides 1-10, 1-9, 2-10, 2-9, 3-10, 1-7, 2-8, 3-9, 4-10, 1-6, 2-7, 3-8, 4-9, and 5-10 of SEQ ID NO:6; nucleotides 1-10, 1-9, 2-10, 1-8, 2-9, 3-10, 1-7, 2-8, 3-9, 4-10, 1-6, 2-7, 3-8, 4-9, and 5-10 of SEQ ID NO:7; and nucleotides 1-10, 1-9, 2-10, 1-8, 2-9, 3-10, 1-7, 2-8, 3-9, 4-10, 1-6, 2-7, 3-8, 4-9, and 5-10 of SEQ ID NO:8.

We initially developed a novel and simplified protocol to both produce mature hepatocytes having functional hepatic enzyme activity from human pluripotent cells and to extend the time during which primary hepatocytes isolated from liver tissue exhibit functional hepatic enzyme activity. The protocol includes the step of transferring an external vector including the DNA sequence coding the microRNA mir-122, an external vector including the DNA sequence coding the microRNA let-7c, or both to a cell. When applied to fetal hepatocytes derived from embryonic stem cells using previously published protocols, this step unexpectedly results in mature hepatocytes that exhibit functional hepatic enzyme activity. When applied to primary hepatocytes isolated from liver tissue, this step unexpectedly results in cells that exhibit functional hepatic enzyme activity at a higher level and for a longer period of time as compared to control primary hepatocytes.

Accordingly, in a first aspect, the disclosure encompasses a method for producing mature hepatocytes having functional hepatic enzyme activity from human pluripotent cells. Human pluripotent cells are cells that have the potential to differentiate into any of the three germ layers: endoderm, mesoderm, or ectoderm. Thus, human pluripotent cells can give rise to any fetal or adult cell type.

The two major types of human pluripotent cells known in the art are human embryonic stem cells and human induced pluripotent stem cells. Human embryonic stem cells are derived from the inner cell mass of the human blastocyst. Induced pluripotent stem cells are a type of pluripotent stem cell artificially derived from a non-pluripotent cell, typically an adult somatic cell, by inducing a "forced" expression of certain genes. Either type of human pluripotent cell can be used in the method.

To perform the method, one or more fetal hepatocytes obtained from one or more human pluripotent cells are differentiated into mature hepatocytes by transferring a microRNA having the functionality of mir-122 or an external vector containing the DNA sequence coding for such a microRNA (e.g. mir-122), a microRNA having the functionality of let-7c or an external vector containing the DNA sequence coding for such a microRNA (i.e. let-7c), or both into the fetal hepatocytes.

The term "external vector" refers to a molecule used as a vehicle to transfer foreign genetic material into another cell. Transfer can occur using a variety of mechanisms known in the art. Two such mechanisms are transduction and transfection.

The term "transduction" refers to the delivery of foreign genetic material to a cell by a virus, and the cells to which the foreign genetic material is delivered are described as "transduced." Transduction in the context of eukaryotic cell culture is well known in the art, and is performed using one of a variety of known viral vectors which can be engineered to include the mir-122 DNA sequence or the let-7c DNA sequence. A non-limiting example of a viral vector for transduction of mir-122 or let-7c into the fetal hepatocytes is a replication-defective retrovirus, such as a lentivirus. A lentivirus vector can integrate its genetic payload into the genome of non-dividing cells. The genetic payload is inserted into the genome of the fetal hepatocyte by the viral integrase enzyme. In this way, the transduction causes substantially increased expression of mir-122 or let-7c within the fetal hepatocytes, which in turn induces differentiation of the fetal hepatocytes into mature hepatocytes. Specific lentiviral vectors that can be used in the method include pEZX-MR01 (Genecoepoeia), as illustrated in Example 1 below, and pEZX-MR03 (Genecoepoeia), as illustrated in Example 7 below. In the case of a lentiviral vector, the DNA sequence that codes for the pre-miRNA and an upstream CMV promoter is transduced into the target cell, and not the cRNA copy, as is the case in other examples of lentiviral facilitated transduction.

Transduction does not always lead to the integration of the transduced DNA into the target cell genome. For example, as opposed to lentiviruses, adenoviral DNA does not integrate into the genome and is not replicated during cell division.

The term "transfection" refers to the delivery of foreign genetic material to a cell by non-viral means. Various methods of transfection are known in the art, and can be used in the disclosed methods. Some transfection methods rely on physical treatment (e.g., electroporation, nanoparticle treatment, or magnetofection), while other methods of transfection rely on chemical materials that are used as carriers of the foreign genetic material.

In the disclosed methods, both viral vectors, such as lentiviral vectors, and non-viral vectors, such as PiggyBac, could be used. For example, a PiggyBac construct that has tet inducible mir-122 expression and a puromycin cassette under EF1A promoter can be used to generate cell lines with inducible mir-122 expression.

Both vectors that integrate the vector DNA into the target cell as well as vectors that deliver the vector DNA episomally are encompassed by the disclosed methods. In the case of cell lines harboring lox sites in the rosa26 locus, the locus can optionally be used to insert the DNA coding for the miRNA via recombination. Because rosa26 is expressed in most cell types (including in embryonic stem cells and hepatocytes), this particular method has the advantage that the transferred DNA would not be silenced after insertion Orion et al. Nature Biotech 2007 25:1477-1482).

Optionally, the fetal hepatocytes into which the vector containing the DNA coding for the microRNA having the functionality of mir-122 and/or let-7c are transferred can be obtained from human pluripotent cells by methods known in the art. For example, human embryonic stem cells may first be differentiated into definitive endoderm cells. There are a number of published protocols for differentiating hES cells into definitive endoderm, most of which culture hES cells in a culture medium that includes activin-A. A non-limiting example of a published protocol to differentiate hES cells to definitive endoderm is that disclosed by J. Cai et al. (Hepatology (2007) 45: 1229-1239).

Once the cells have been differentiated into definitive endoderm, the cells may be further differentiated into hepatic endoderm. Again, there are a number of published protocols for differentiating definitive endoderm cells into hepatic endoderm, most of which culture the definitive endoderm cells in a culture medium that includes both fibroblast growth factor-4 (FGF4) and bone morphogenetic protein-2 (BMP2). A non-limiting example of a published protocol to differentiate definitive endoderm to fetal hepatic endoderm is that disclosed by J. Cai et al. (Hepatology (2007) 45: 1229-1239).

Next, the hepatic endoderm may be differentiated into fetal hepatocytes. Various combinations of growth factors and other chemicals can be added to the culture medium for various durations of time to differentiate the hepatic endoderm into fetal hepatocytes. Factors and chemicals that can be used in this step include without limitation hepatocyte growth factor, oncostatin-M and dexamethasone. A non-limiting example of a published protocol to differentiate hepatic endoderm to fetal hepatocytes is that disclosed by J. Cai et al. (Hepatology (2007) 45: 1229-1239).

As used herein, the term "fetal hepatocyte" refers to a putative hepatocyte that is differentiated from human pluripotent cells, such as hES cells or hiPS cells, and exhibits a morphology similar to that of primary hepatocytes, that secretes albumin and expresses one or more markers associated with liver cells, but that does not express one or more of the liver proteins albumin, alpha-1-antitrypsin (AAT), tyrosine aminotransferase (TAT), CYP1A2, CYP7A1 or CYP3A4 at a level that is at least equal to the expression level of these liver proteins in fresh primary hepatocytes, or that cannot metabolize drugs using a standard in vitro metabolism test. To determine whether a putative hepatocyte is a true hepatocyte rather than a fetal hepatocyte, gene expression levels are measured quantitatively and compared to the gene expression in cultured fresh primary hepatocytes. Such quantitative methods are known in the art, and include, for example, quantitative real time PCR (QRT PCR).

Standard in vitro metabolism tests are well known in the art, and include the introduction of a drug substrate into the putative hepatocyte culture. Metabolism of the substrate can be confirmed by testing the medium for known substrate metabolites, which can be detected and quantified by known methods, such as mass spectrometry. Non-limiting examples of common substrates used in standard metabolism tests include omeprazole, rifampicin, phenobarbital, coumarin, caffeine, diclofenac, bupropion, S-mephenytoin, dextromethorphan, and verapamil.

Some of these substrates are also known inducers of cytochrome C450 enzyme gene expression, and enzyme induction assays can be used in conjunction with quantitative expression assays to confirm putative hepatocyte function. For example, omeprazole induces the CYP1A2 enzyme in true hepatocytes, but not in fetal hepatocytes, and rifampicin induces the CYP3A4 enzyme in true hepatocytes, but not in fetal hepatocytes.

As used herein, the term "primary hepatocyte" refers to a cultured liver cell that has been isolated directly from liver tissue.

As used herein, the phrase "having functional hepatic enzyme activity" means that the cell in question expresses one or more of the liver proteins albumin, alpha-1-antitrypsin (AAT), tyrosine aminotransferase (TAT), CYP1A2, CYP7A1 or CYP3A4 at a level that is at least equal to the expression level of these liver proteins in fresh primary hepatocytes. Furthermore, for a cell to have "functional hepatic enzyme activity," expression levels for the three CYP genes 1A2, 3A4 and 7A1 are all at least 70% of the expression levels in fresh primary hepatocytes.

As used herein, the term "mature hepatocyte" refers to putative hepatocytes exhibiting functional hepatic enzyme activity. In addition, mature hepatocytes can metabolize one or more drugs, as shown by a standard in vitro metabolism test, and exhibit cytochrome C450 enzyme induction in the presence of one or more known inducers.

The disclosure also encompasses a method for maintaining the functional hepatic enzyme activity of primary hepatocytes in culture. Fresh primary hepatocytes are obtained by isolating and culturing liver cells obtained from liver tissue. A microRNA having the functionality of mir-122 or an external vector including the DNA sequence coding for such a microRNA is then transferred into the hepatocytes. As with the methods using fetal hepatocyte targets as described above, a variety of methods known in the art can be used to facilitate the transfer. The primary hepatocytes produced by this method maintain higher levels of functional hepatic enzyme activity after several days of culture than do primary hepatocytes that have not been transduced.

The disclosure also encompasses methods of using the hepatocytes produced by the disclosed methods in toxicity testing and in treating patients having a liver disorder. Apart from testing the toxicity of the compound on the hepatocytes themselves, the hepatocyte media containing the metabolite of the compound may be taken and put on cultures of non-hepatocytes. For example, liver cell metabolites may be subsequently tested on cardiomyocytes (for cardiotoxicity testing) or on cultures of neurons (for neurotoxicity testing). Testing on the non-hepatocyte cells may occur either in a co-culture, or with a conditioned medium. This is a useful method for testing certain drugs that are not toxic in themselves, but which may be converted to a toxic form by the liver. For example, certain liver metabolites of non-toxic compounds are known to block the hERG channel in the heart, causing arrhythmias. However, the method is not limited by this example, and can be broadly applied to a variety of non-hepatocyte cell types.

Such methods include the step of monitoring the hepatocytes or non-hepatocytes for signs of potential toxicity. The cells need not be directly observed, and this step encompasses a variety of methods for assaying potential cellular damage or dysfunction caused by exposure to a test compound. Monitoring for signs of toxicity may include, without limitation, testing for the levels of certain biomarkers or gene expression products, testing cellular function, and directly observing the structure of the cells. As a non-limiting example, elevated levels of certain biochemical markers (e.g., alanine transferase, alkaline phosphotase, and bilirubin) can indicate toxicity in hepatocytes. Furthermore, cellular apoptosis, changes in cellular morphology, or the transformation of cells into a neoplastic form may result from induced toxicity. The method is not limited to any particular monitoring technique, and encompasses any such techniques used in the art.

Regarding methods of treating liver disorders, the hepatocytes produced by the disclosed methods may be used either short term or long term in patients wherein an orthotopic liver transplant would be desirable. Transplantation of functional hepatocytes may save many lives, as there is a severe shortage of livers for transplantation, resulting in large number of deaths to patients on liver transplant waiting lists. For example, functional hepatocytes could be used for treatment of liver metabolic disorders such as alpha-1-antitrypsin deficiency and Wilson's disease, where in severe cases, orthotopic liver transplant is currently the only recourse. Furthermore, in cases of acute liver damage (such as from drug overdose), hepatocyte transplantation may also save lives. Finally, hepatocyte transplantation may help people on transplant waiting lists live long enough to receive an organ (i.e., bridge transplantation).

The inventors demonstrate herein that the hESC-derived hepatocytes expressing let-7c do not support the in vitro replication of hepatitis viruses, such as HBV and HCV. Thus, such hepatocytes (and other agents containing let-7c or capable of upregulating let-7c) could be used to treat liver inflammation caused by hepatitis infection, or to reduce progression to disorders secondary to such infections, such as cirrhosis and liver cancer.

The disclosure also encompasses isolated hepatocytes that maintain levels of enzymes at a certain level for up to 19 days for certain enzymes, regardless of the hepatocyte source. Specifically, after being cultured for at least nine days, the isolated hepatocytes maintain expression levels of albumin and tyrosine aminotransferase (TAT) that are at least 80% of the level that was exhibited when the culture was established, an expression level of CYP1A2 that is similar to when the culture was established and an expression level of CYP3A4 and CYP7A1 that is greater than when the culture was established.

The disclosure also encompasses an in vitro method for supporting the replication of a hepatitis virus. The method includes the step of exposing one or more mature hepatocytes prepared according to the methods described herein to a hepatitis virus. The hepatitis virus replicates within the one or more mature hepatocytes. In certain embodiments, the hepatitis virus is hepatitis B virus (HBV) or hepatitis C virus (HCV).

Viral hepatitis is liver inflammation due to a viral infection. It may be present in acute or chronic forms. The most common causes of viral hepatitis are the five unrelated hepatotropic viruses known as Hepatitis A (HAV), Hepatitis B (HBV), Hepatitis C (HCV), Hepatitis D (HDV), and Hepatitis E (HEV). Hepatitis viruses impact patient health through a complex interplay with the host, and different hosts react differently upon exposure to the same hepatitis virus.

Currently, there are no in vitro models that can be successfully used to study hepatitis liver infection and possible treatments for such infection. As discussed previously, primary hepatocyte cultures are difficult to obtain, and cultured hepatocytes tend to rapidly lose their characteristic structure and function. However, the inventors have demonstrated that cultures made up of mature hepatocytes produced from human embryonic stem cells using the disclosed method support the replication of HBV. Thus, the cells can be used to form cultures for the study of hepatitis infection and treatment.

The inventors have demonstrated that in hepatocellular carcinoma tissue, expression levels of both let-7c and mir-122 are correlated with the differentiation state of the tissue, with highly differentiated tissue having greater expression of these miRNAs. Normal tissue exhibits the highest miRNA expression. Accordingly, the disclosure also encompasses a method of treating hepatocellular carcinoma by administering to a patient having this condition (a) a miRNA having the functionality of let-7c, a miRNA having the functionality of mir-122, or both; or (b) an agent that upregulates the expression of the microRNA mir-122, the expression of the microRNA let-7c, or the expression of both the microRNA let-7c and the microRNA mir-122.

The following Examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Example 1

Expression of mir-122 in Human Embryonic Stem Cell-Derived Hepatocytes Induces Cytochrome P450 and Other Liver Genes, Facilitates Highly Efficient Drug Processing, and Supports In Vivo Replication of HBV and HCV Introduction Hepatocytes differentiated from human embryonic stem cells (hES cells) are fetal in nature i.e., they do not express cytochrome P450 genes or metabolize drugs in vitro. Here we report that miR-122, an abundant adult liver-expressed miRNA, when expressed in fetal hepatocytes derived from hES cells, induces increased expression of cytochrome P450 and other mature liver-specific genes. Further, the resulting cells metabolize drugs highly efficiently, thus validating their usefulness in drug metabolism and toxicity testing.

Cultured hepatocytes are an indispensable tool for testing drug metabolism and toxicity. Human primary hepatocytes are ideal for such purposes but rapidly lose expression of cytochrome P450 enzymes and their capability for xenobiotic metabolism in vitro. Moreover, they are not readily available, do not proliferate in culture and vary in their drug response between batches isolated from different individuals. Here we report for the first time the generation of mature and functional hepatocytes from hES cells by expressing an adult liver specific miRNA, miR-122, within the hES cells during differentiation. The resulting miR-122 expressing hepatocytes metabolize drugs highly efficiently, are genetically consistent and could be generated in large volumes. Thus, they would be very useful to the pharmaceutical industry. Such hepatocytes would also be useful as therapeutics, such as in the transplantation and generation of bioartificial livers, as well in the study and treatment of inherited metabolic disorders of the liver.

Summary of Methods and Results

Many published protocols produce putative hepatocytes from hES cells, but those hepatocytes lack functional hepatic enzyme activity. These protocols first generate definitive endoderm by culturing hES within a culture medium containing activin-A. Next, hepatic endoderm is generated by culturing the definitive endoderm cells in a culture medium containing bone morphogenetic protein 2 (BMP2) and fibroblast growth factor 4 (FGF4). Finally, cells having hepatocyte morphology are generated using various combinations of several growth factors and chemicals within the culture medium for various durations. Factors and chemicals used in this final step may include hepatocyte growth factor, oncostatin-M, and dexamethasone.

Figure 1B:
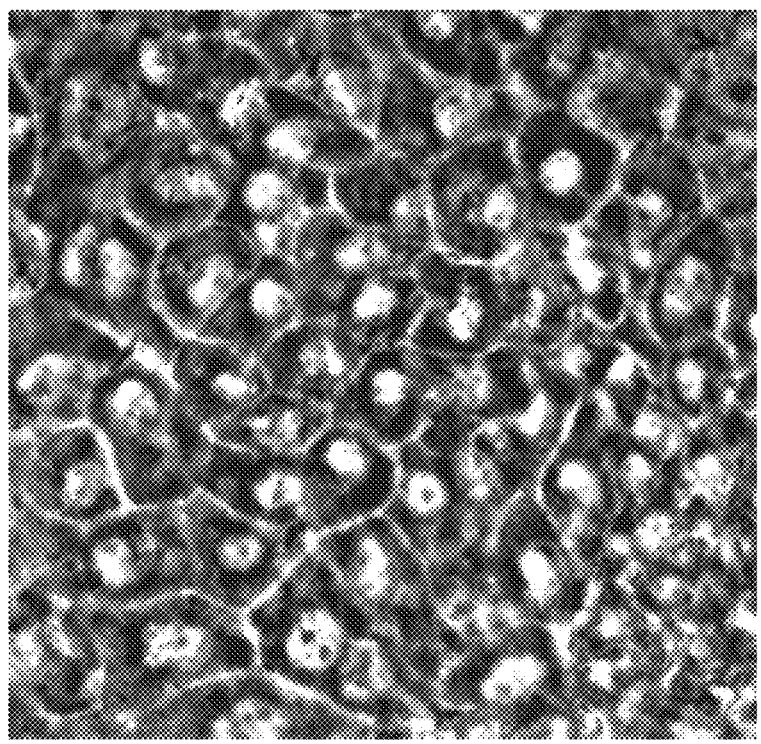

We broadly followed one such protocol (see J. Cai et al., Hepatology (2007) 45: 1229-1239) to differentiate H1 hES cells (see J. A. Thomson et al., Science (1998) 282: 1145-1147) to fetal hepatocytes that morphologically resembled mature human liver derived hepatocytes (See FIG. 1). We first characterized these hepatocytes by profiling their global gene expression through Illumina mRNA-Seq. Although hepatocyte specific genes such as Keratins 8 and 18 were highly expressed in the hES-derived fetal hepatocytes, they did not express any functional Cytochrome P450 genes (such as CYP1A2 and CYP3A4), within the level of detection. At the same time, the fetal hepatocytes expressed a fetal marker, alpha-fetoprotein, at very high levels, as well as a cholangiocyte specific keratin, KRT7, indicating that these cells were more fetal and undifferentiated in nature than mature and functional. See Table 1.

TABLE 1

Gene expression of human liver hepatocytes, the hES cell-derived fetal hepatocytes, and the H1 hES cells from which the fetal hepatocytes were derived. Expression units are transcripts per million (TPM).

| Gene | H1 hES Cells | hES cell-derived fetal hepatocytes | Human liver Hepatocytes |
|---|---|---|---|
| KRT8 | 44.85 | 400.31 | 30.84 |
| KRT18 | 186.44 | 849.11 | 86.34 |
| KRT7 | 3.06 | 49.73 | 1.51 |
| ALB | 5.95 | 52.78 | 112362.39 |
| AFP | 13.36 | 4767.10 | 13.29 |
| CYP1A2 | 4.44 | 28.26 | 101.30 |
| CYP3A4 | 0.80 | 1.93 | 3024.18 |

We next profiled the miRNA expressions of hES derived hepatocytes and primary hepatocytes using Illumina global small RNA sequencing. Most miRNAs that were expressed abundantly in human liver-derived hepatocytes were also present in the hES-derived fetal hepatocytes, with the notable exception of miR-122 and let-7c (see Table 2). Of these two miRNAs, miR-122 is known to be a liver-specific miRNA,

TABLE 2 miRNA expression of human liver hepatocytes and hES cell-derived fetal hepatocytes. These reported values are numbers of mature miRNA tags in a sample. Although no normalization was done on the samples, the libraries were prepared with same starting RNA amounts.

| miRNA | Liver derived hepatocytes | hES cell-derived fetal hepatocytes |
|---|---|---|
| hsa-let-7c | 63269 | 790 |
| hsa-miR-122 | 60961 | 96 |
| hsa-miR-378c | 36754 | 8569 |
| hsa-miR-143 | 32569 | 11412 |
| hsa-miR-148a | 29138 | 15562 |
| hsa-miR-21 | 23047 | 161988 |

Figure 2:
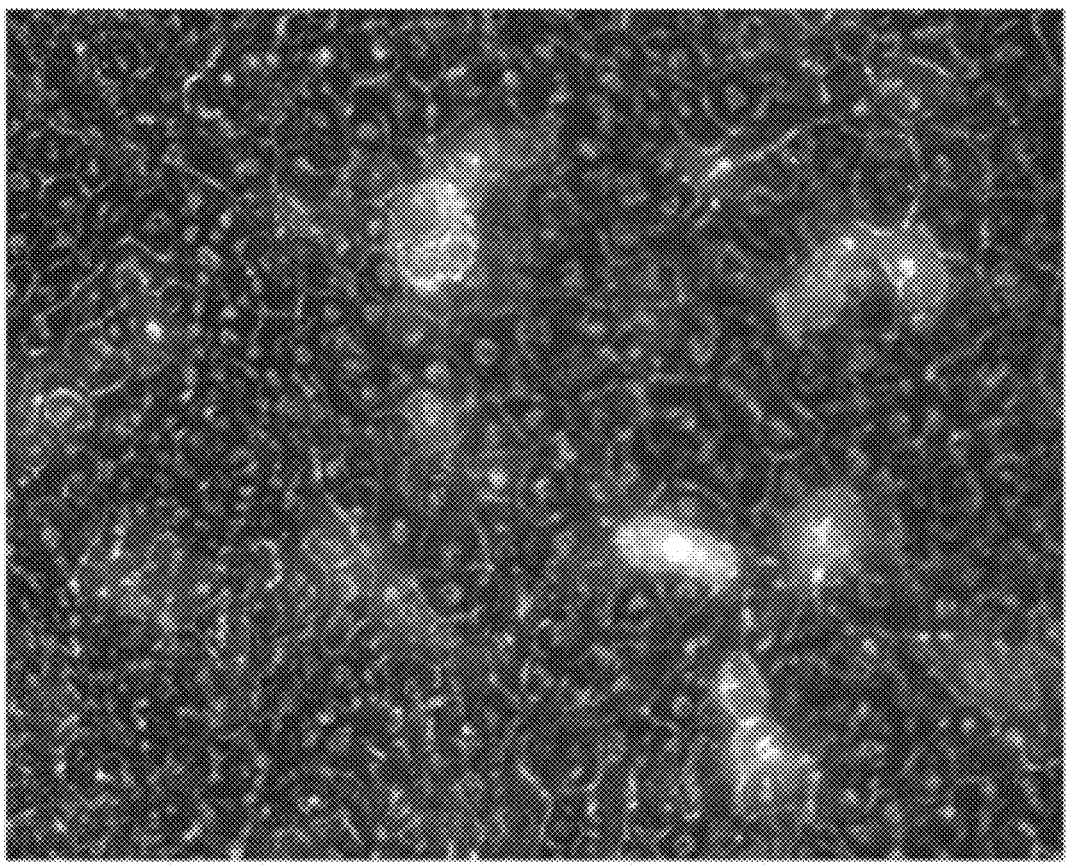
FIG. 2 shows successful lentiviral transduction of mir-122 into human embryonic stem cell-derived hepatocytes. GFP expression indicates successful transduction of a cell. About 5% of the cells were successfully transduced.
Figure 3A:
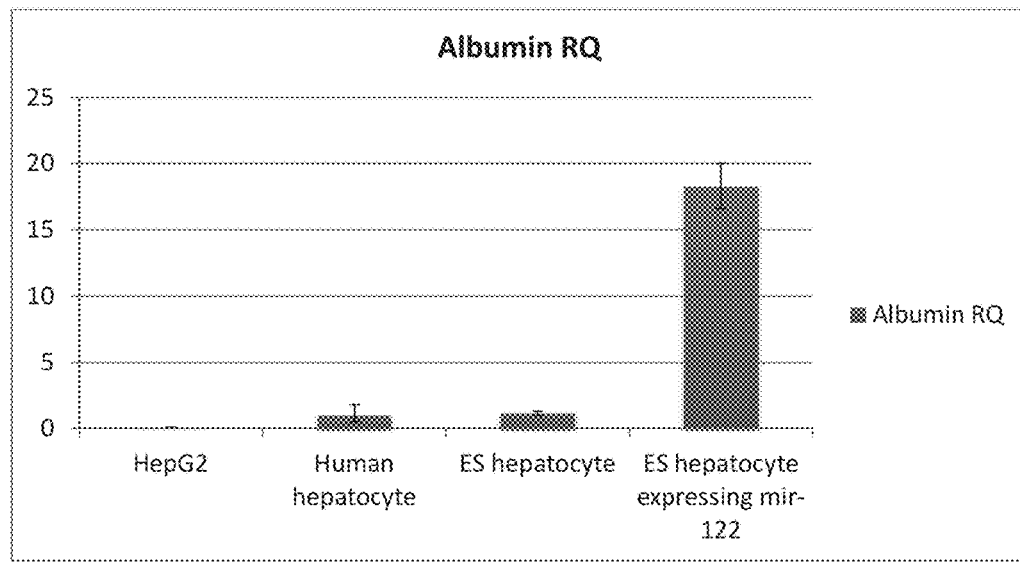
FIGS. 3A through 3F are bar graphs showing that expression of mir-122 in human embryonic stem cell-derived hepatocytes induces expression of albumin (FIG. 3A), alpha-1 antitrypsin (AAT) (FIG. 3B), tyrosine aminotransferase (TAT) FIG. 3C), and the CYP P450 enzymes CYP1A2 (FIG. 3D), CYP3A4 (FIG. 3E) and CYP7A1 (FIG. 3F). Expression of these enzyme levels was also measured in HepG2 (a human hepatoma cells line), human hepatocytes and in negative control cells (fetal hepatocytes that were not transduced). Expression was measured by quantitative PCR. Indicated expression levels (on the Y axis) are GAPDH normalized gene expression values called RQ values (relative quantity values). Error bars indicate RQ min and RQ max values calculated on 1 standard deviation. All RQ, RQ min and RQ max values were calculated with ViiA7 software on Applied Biosystems QPCR system.
Figure 3B:
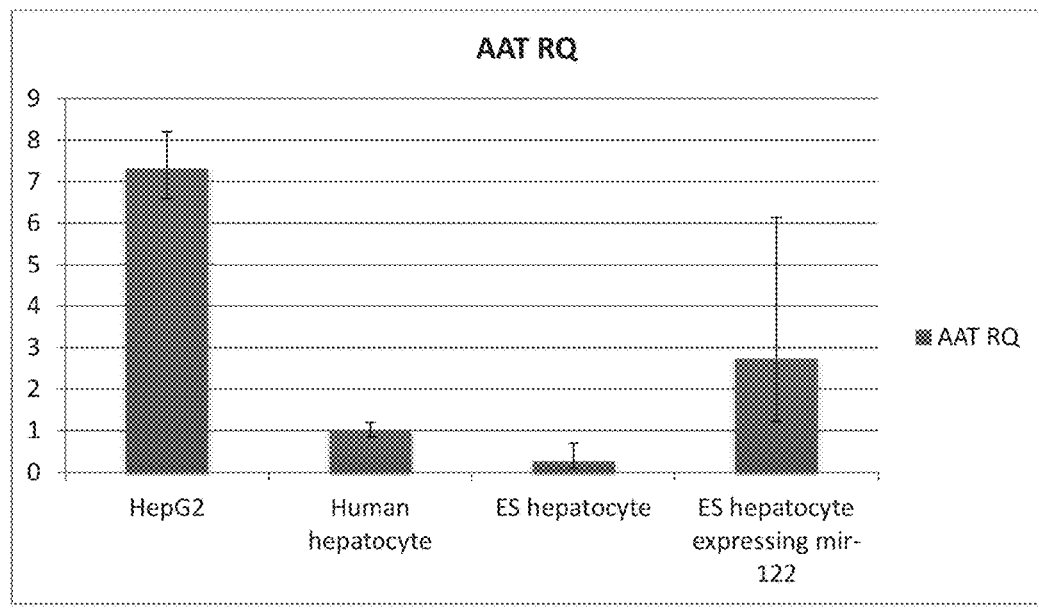
Figure 3C:
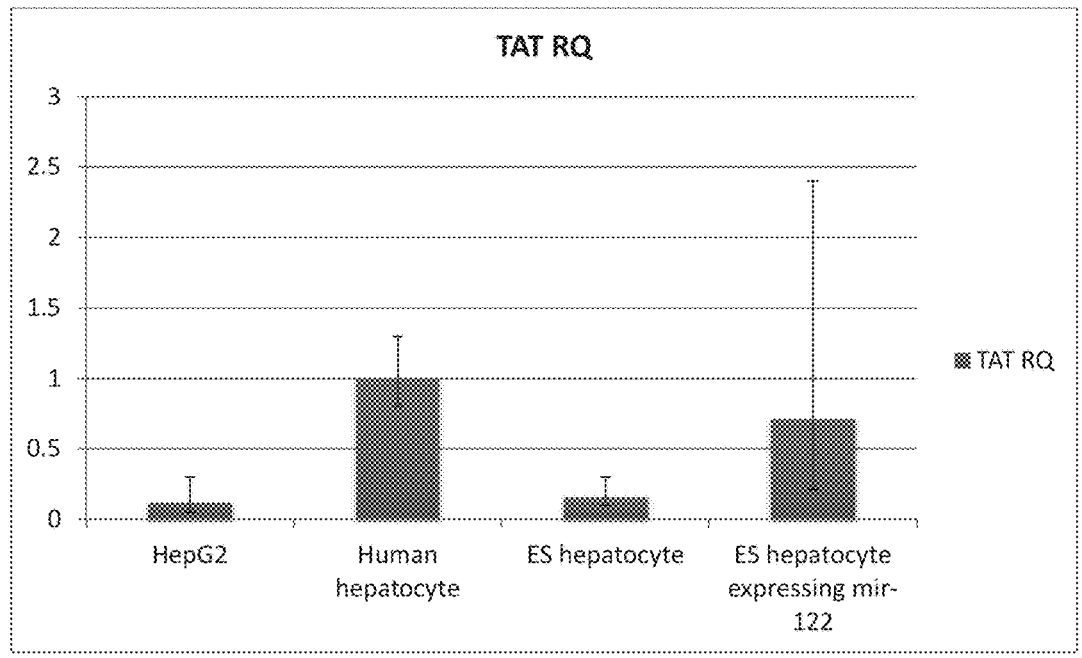
Figure 3D:
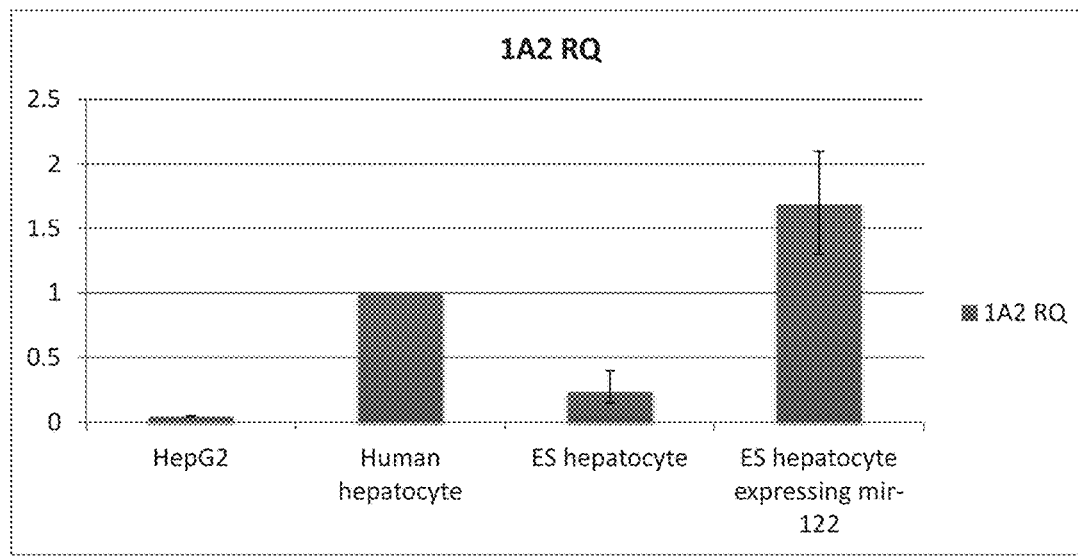
Figure 3E:
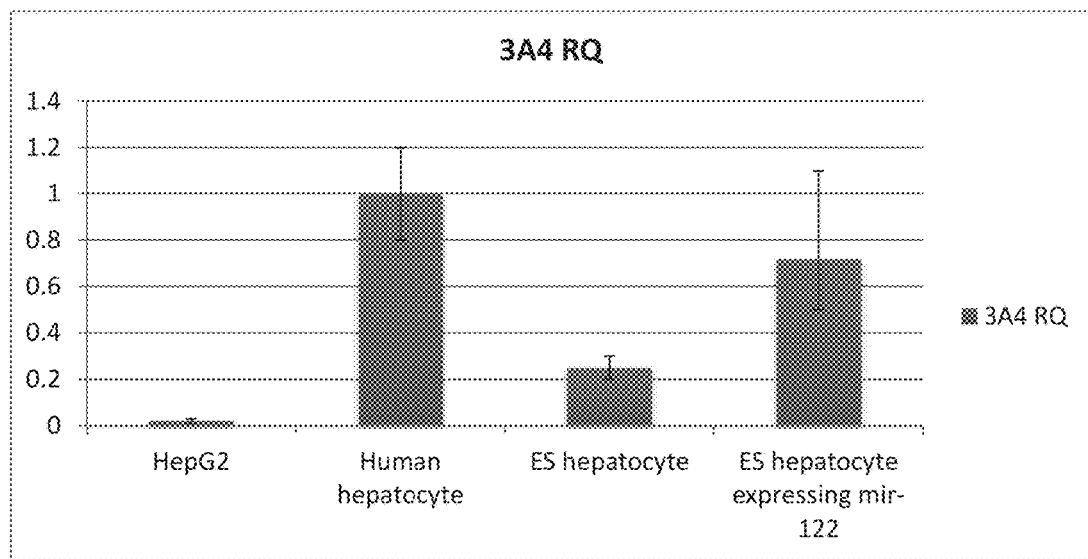
Figure 3F:
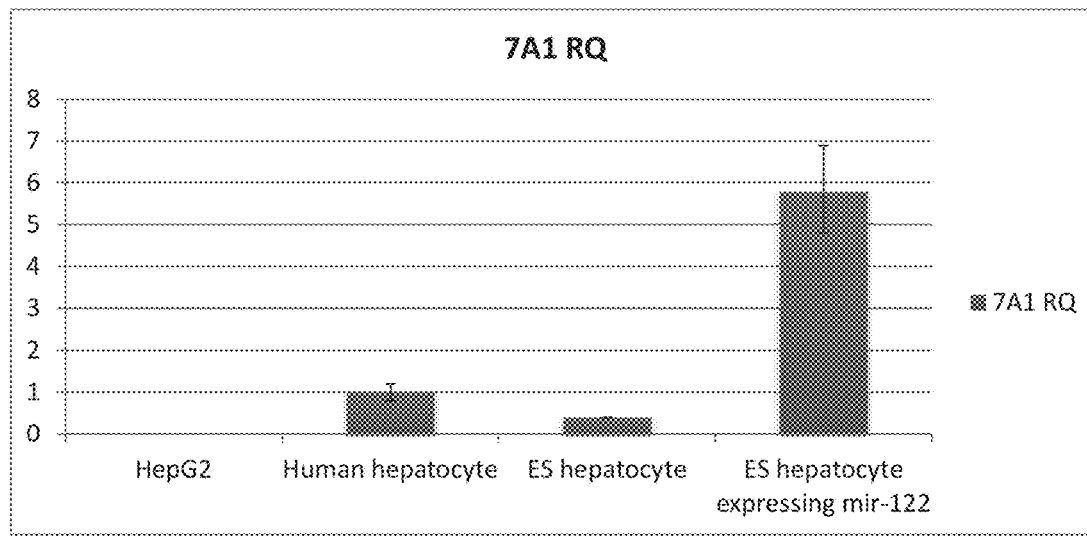

We next determined whether forced expression of mir-122 in the hES cell-derived fetal hepatocytes could program these cells to a more mature differentiated state. We expressed mir-122 in the fetal hepatocytes by lentiviral transduction. Using this method, we achieved ~5% transduction efficiency (see FIG. 2 GFP positive cells).

These GFP positive cells were then FACS sorted, and RNA was isolated for QPCR measurements of functional genes. Quantitative PCR measurement showed significant up-regulation of functional genes in cells expressing miR-122 (see FIG. 3).

Figure 4:
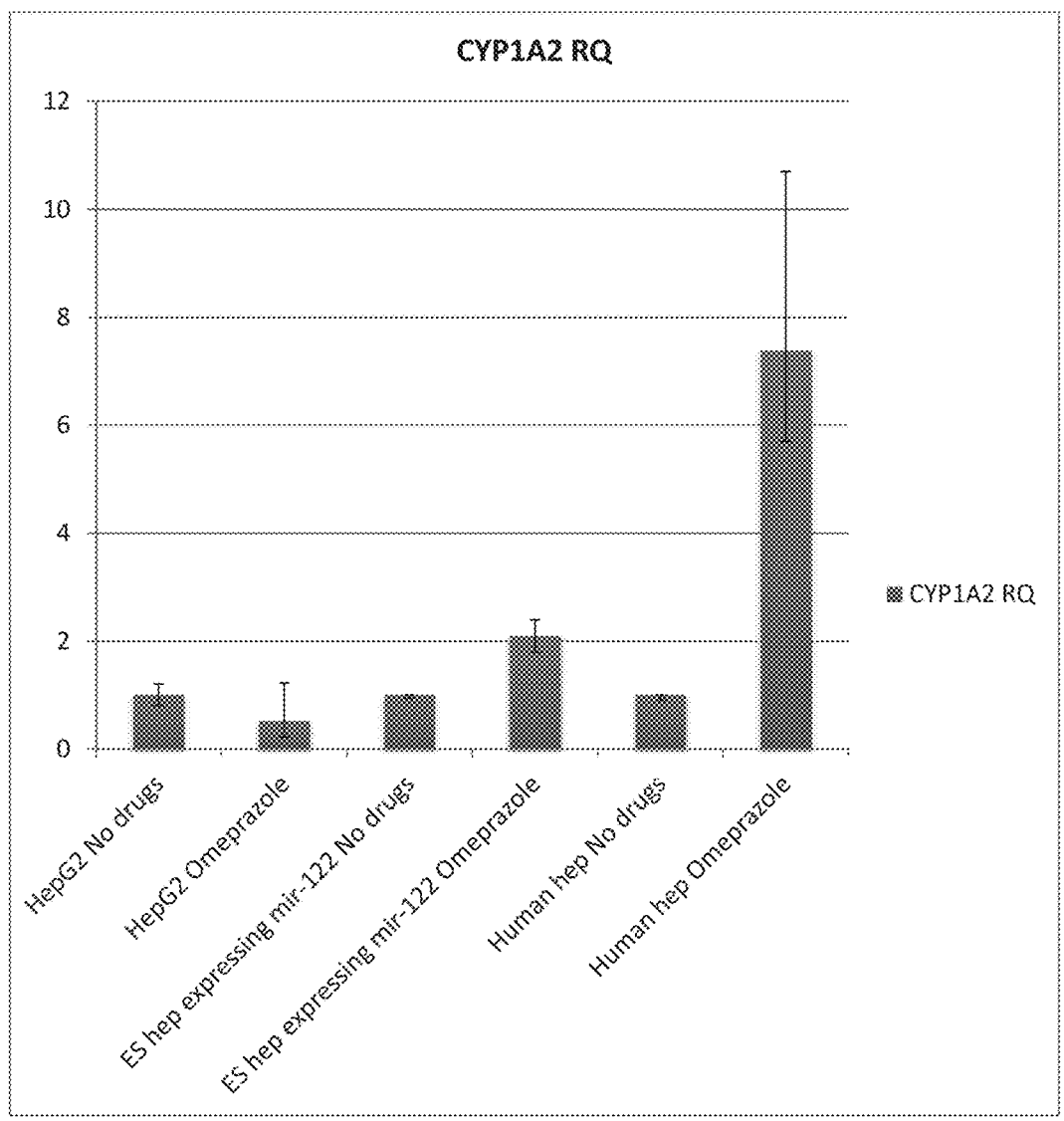
FIG. 4 is a bar graph showing that mature embryonic stem cell-derived hepatocytes expressing mir-122 exhibit induction of CYP1A2 by omeprazole. Induction of this enzyme was also measured in HepG2 human hepatocytes and in fresh primary human hepatocytes. Expression was measured by quantitative PCR, and the expression levels are shown as GAPDH normalized gene expression values (RQ values or relative quantity values. Error bars indicate RQ min and RQ max values).
Figure 5:
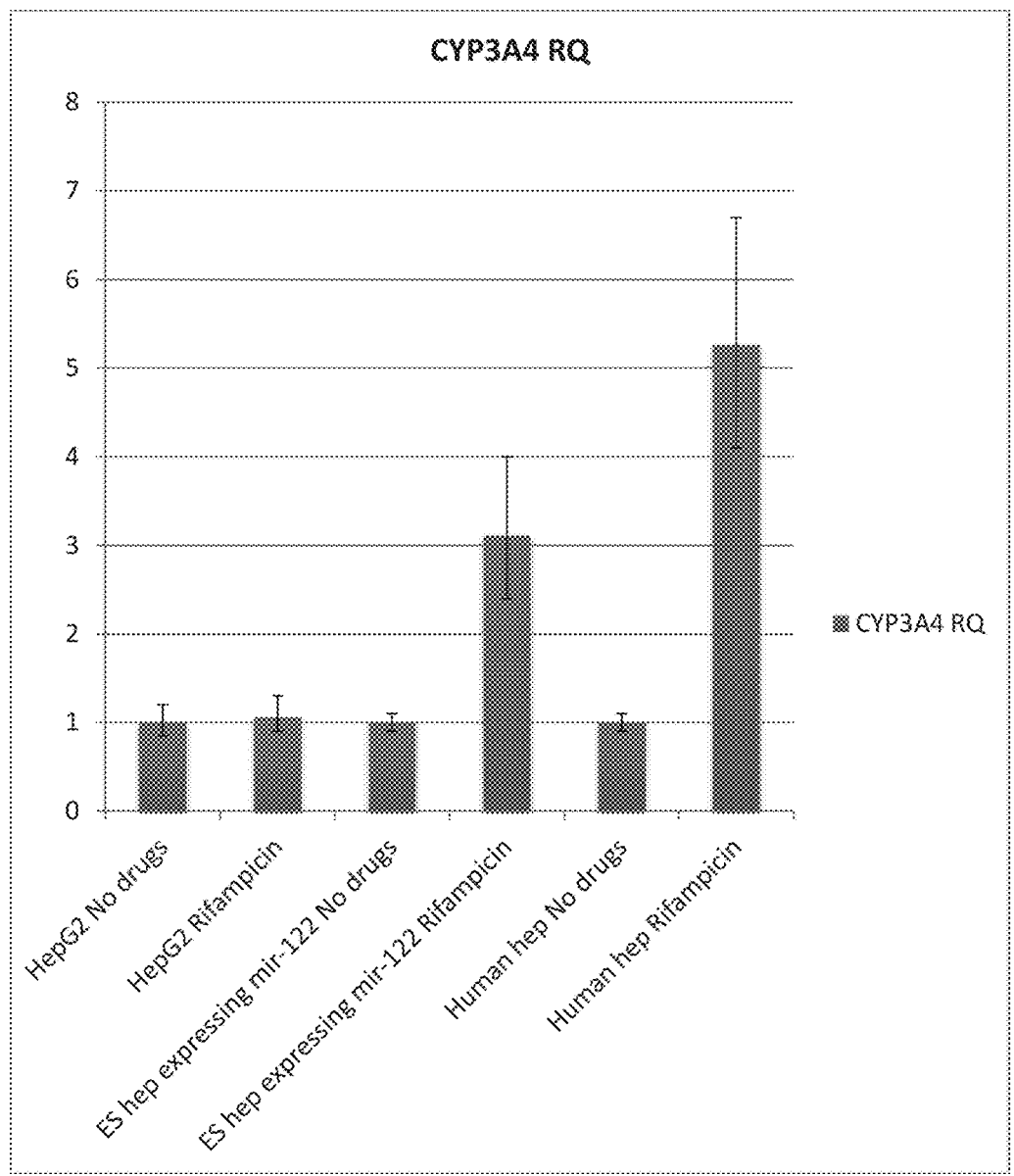
FIG. 5 is a bar graph showing that mature embryonic stem cell-derived hepatocytes expressing mir-122 exhibit induction of CYP3A4 by rifampin. Induction of this enzyme was also measured in HepG2 human hepatocytes and in fresh primary human hepatocytes. Expression was measured by quantitative PCR, and the expression levels are shown as GAPDH normalized gene expression values (RQ values or relative quantity values. Error bars indicate RQ min and RQ max values).
Figure 6A:
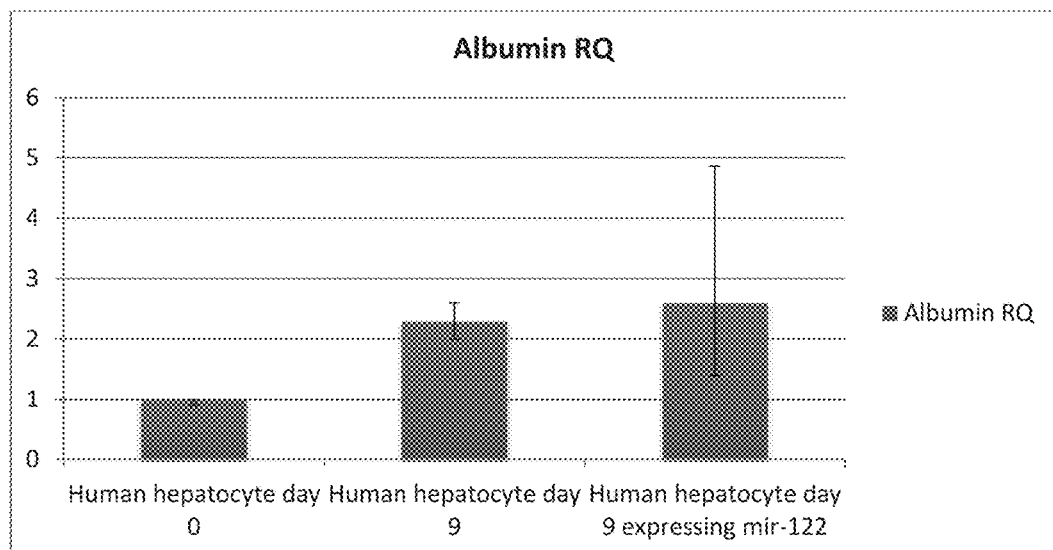
FIGS. 6A through 6E are a bar graphs showing that lentivirus mediated DNA transfer to primary hepatocytes derived directly from liver tissue results in improved hepatic protein expression over time, as compared to control primary hepatocytes. Expression is shown for albumin (FIG. 6A), tyrosine aminotransferase (TAT) (FIG. 6B), and the CYP 450 enzymes CYP1A2 (FIG. 6C), CYP3A4 (FIG. 6D) and CYP7A1 (FIG. 6E). Expression was measured by quantitative PCR, and the reported values were normalized by GAPDH expression (RQ or relative quantity values, error bars representing standard error, RQ min and RQ max). Expression values are shown for each gene at the time the culture was established (0 day) and 9, 13 or 19 days later.
Figure 6B:
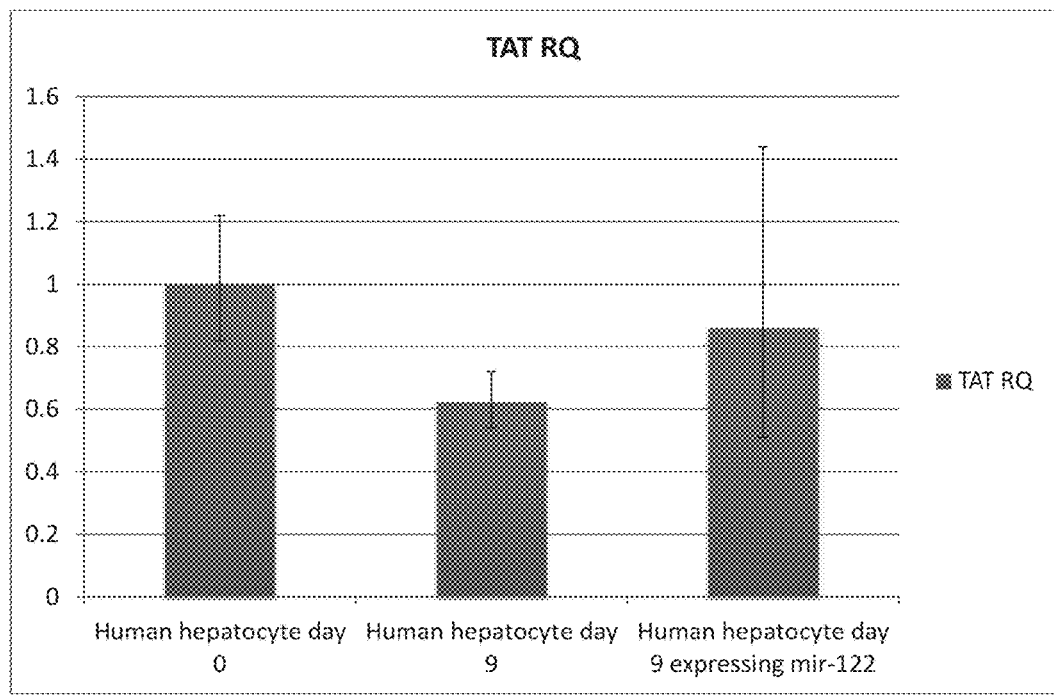
Figure 6C:
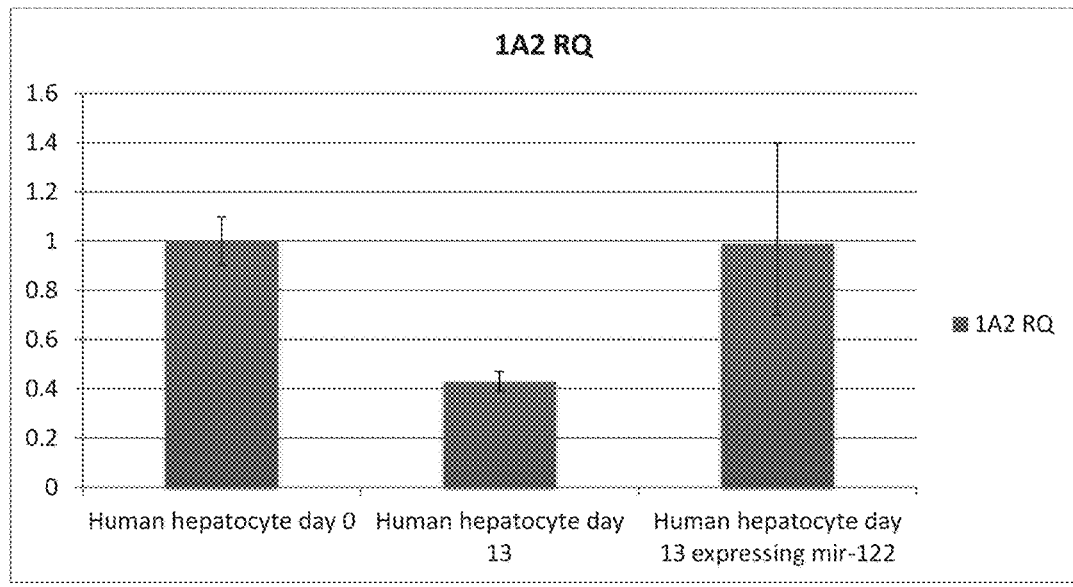
Figure 6D:
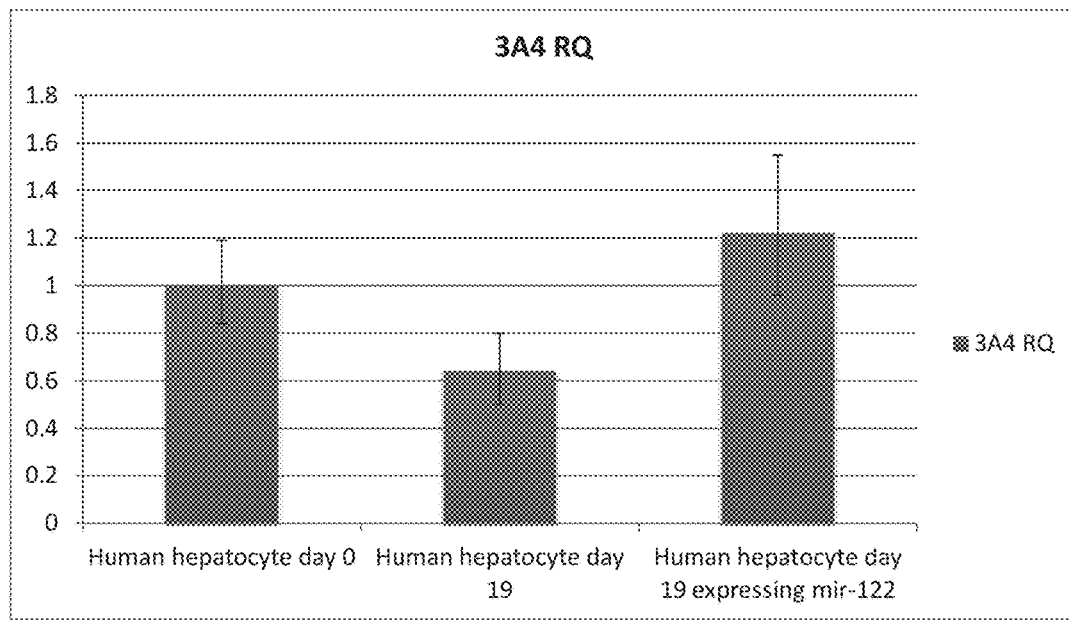
Figure 6E:
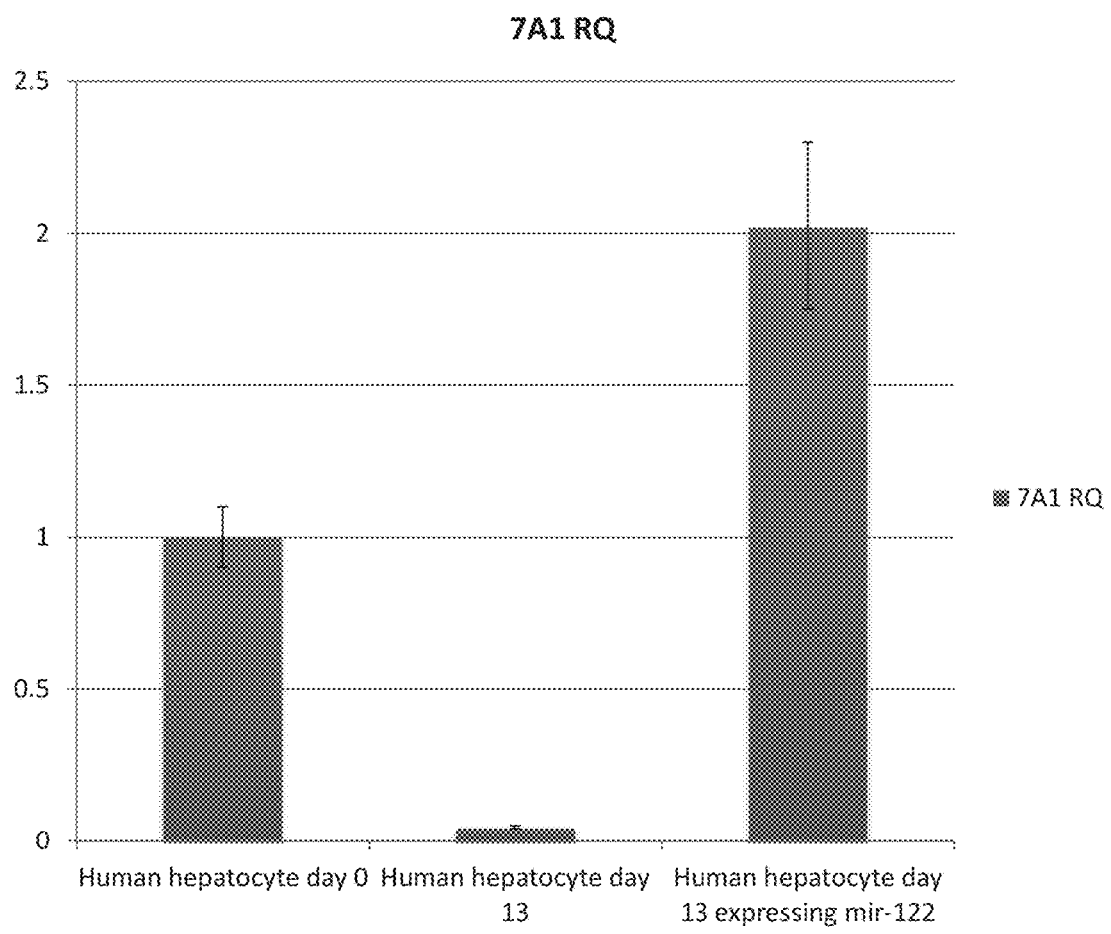

We next performed assays to determine if the transduced cells were indeed functional and able to metabolize drugs. We tested a prototypical drug, omeprazole, on these cells and found that the addition of omeprazole substantially up-regulated the expression of CYP1A2, the enzyme that is responsible for metabolizing this drug (see FIG. 4). We also tested a second prototypical drug, rifampicin (rifampin), on these cells and found that the addition of rifampicin substantially up-regulated the expression of CYP3A4, the enzyme that is responsible for metabolizing this drug (see FIG. 5). These results suggest that expression of mir-122 indeed confers functionality to the transduced hES cell-derived hepatocytes.

Currently, there is a lack of systems that are capable of supporting the in vitro replication of hepatitis viruses, such as HBV and HCV, which are major causes of liver disease. We next tested the mir-122 expressing mature hepatocytes obtained as described above, and demonstrated that cultures of these mature hepatocytes support the replication of HBV (see Example 5 below).

Materials and Methods

Cells and Hepatocyte Differentiation.

H1 hES cells (J. A. Thomson et al., Science (1998) 282: 1145-1147) cultured in E8 medium (Chen et al., 2011 Nature Methods 8(5) 424-9) were differentiated to fetal hepatocytes lacking functional hepatic enzyme activity following a previously published protocol (see J. Cai et al., Hepatology (2007) 45: 1229-1239), with some modifications. Briefly, the hES cells at approximately 50% confluency were treated with 0.5 mg/ml Albumin fraction V (Sigma) and 100 ng/ml Activin A (Sigma) for 3 days. On the second day of treatment, 0.1% Insulin-transferrin-Selenium (Sigma) was added, and on the third day of treatment, 1.0% Insulin-transferrin-Selenium (Sigma) was added. From day four to day eight, the cells were treated with 30 ng/ml FGF4 (R&D Systems) along with 20 ng/ml BMP2. From days nine through thirteen, 20 ng/ml HGF (R&D Systems) were added to the medium, and finally, the cells were treated for five days with 10 ng/ml Oncostatin M (R&D Systems) and 0.1 µM Dexamethasone (Sigma). Throughout differentiation, hepatocyte growth medium (Promocell) was used as a base medium and cells were kept on Matrigel™ coated plates. Male human hepatocytes were obtained for comparison studies (Celsis).

RNA Profiling.

Total RNA was isolated with Trizol (Invitrogen) and treated with Dnase I. miRNA and mRNA were profiled by Illumina sequencing. MiRNA libraries were made following Illumina's protocol and mRNA libraries were prepared using the T7LA protocol (S. Sengupta et al., BioTechniques (2010) 49(6): 898-904).

Lentiviral miRNA Expression.

Mir-122 was transduced into the hES derived cells having hepatocyte morphology by a lentiviral vector pEZX-MR01 (Genecoepoeia). Approximately ~5% of cells were transduced, as measured by GFP expression.

Mass Spectrometry.

Omeprazole and rifampicin (also known as rifampin; Sigma) were added to DMEM at 100 µM and 10 µM respectively for 3 days. The resulting medium was analyzed by mass spectrometry. Metabolites of the tested drugs, omeprazole sulfone (Santa Cruz Biotechnology), 5-hydroxy omeprazole (Cachesyn), and desacetyl rifampicin (Santa Cruz Biotechnology) were dissolved in DMEM to prepare standard curves.

Example 2

Expression of mir-122 Extends Functional Gene Expression in Human Hepatocytes Derived from Liver Tissue Primary human hepatocytes isolated from liver tissue lose expression of functional genes in culture over time. In this example, we show that overexpression of mir-122 in cultured human hepatocytes can induce expression of functional genes over an extended period of time.

We cultured primary human hepatocytes (both control hepatocytes and hepatocytes into which vectors were transferred to express mir-122). Mir-122 was transduced into these primary hepatocytes using the lentiviral vector PEZX-MR01. GFP expressing cells were FACS sorted before RNA isolation and gene expression measurements using QPCR.

Results

As shown in FIGS. 6a through 6e, mRNA levels for all functional genes except albumin decreased in the control hepatocytes cultured for 9 days or more, as compared to fresh, uncultured hepatocytes (day 0). Unexpectedly, all of those genes regained their expression in primary hepatocytes transfected to overexpress mir-122. Specifically, all the CYP genes were expressed at equal or greater amount in mir-122 expressing cells compared to fresh hepatocytes (day 0) whereas their expression dropped in non-transduced primary hepatocytes.

Example 3

Expression of hESC-Derived Mature Hepatocytes Transduced with mir-122: A Side by Side Comparison with Fresh Human Hepatocyte Expression In this example, we performed a QRT PCR comparison of the gene expression levels of the mature hepatocytes produced from human embryonic stem cells according to the procedure outlined in Example 1 (ES hepatocyte expressing mir-122), the expression levels for the same proteins in human primary hepatocytes (Human hepatocyte), the expression levels for the same proteins in the fetal hepatocytes before transduction (ES hepatocyte), and the expression levels for the same proteins in HepG2 cells.

All functional genes measured in the transduced mature hepatocytes (albumin, alb; tyrosine aminotransferase, tat; CYP1A2; CYP7A1; CYP3A4; alpha-1 antitrypsin, aat) exhibited equal or greater expression than in primary hepatocytes (see FIGS. 3a through 3f).

Example 4

Transfection of Transposon Vector to Facilitate mir-122 Overexpression and Extend Functional Gene Expression in Human Hepatocytes Derived from Liver Tissue In this example, we show that a different vector and delivery approach to the overexpression of mir-122 in cultured human hepatocytes can induce expression of functional genes over an extended period of time. Specifically, we used a PiggyBac transposon vector into which was cloned the DNA coding sequence for pre-mir-122, and introduced the vector into the human hepatocytes by electroporation. In this PiggyBac transposon mediated transfer, the coding DNA (here mir-122) gets integrated into the cellular genome in multiple locations.

The PiggyBac clone pB-mir-122-hAlb-puro carries a puromycin resistance gene and an inducible mir-122 expression cassette. When electroporated into the cells, the region between the 5' and 3'UTR was incorporated into the cellular genome.

Methods.

Figure 7:
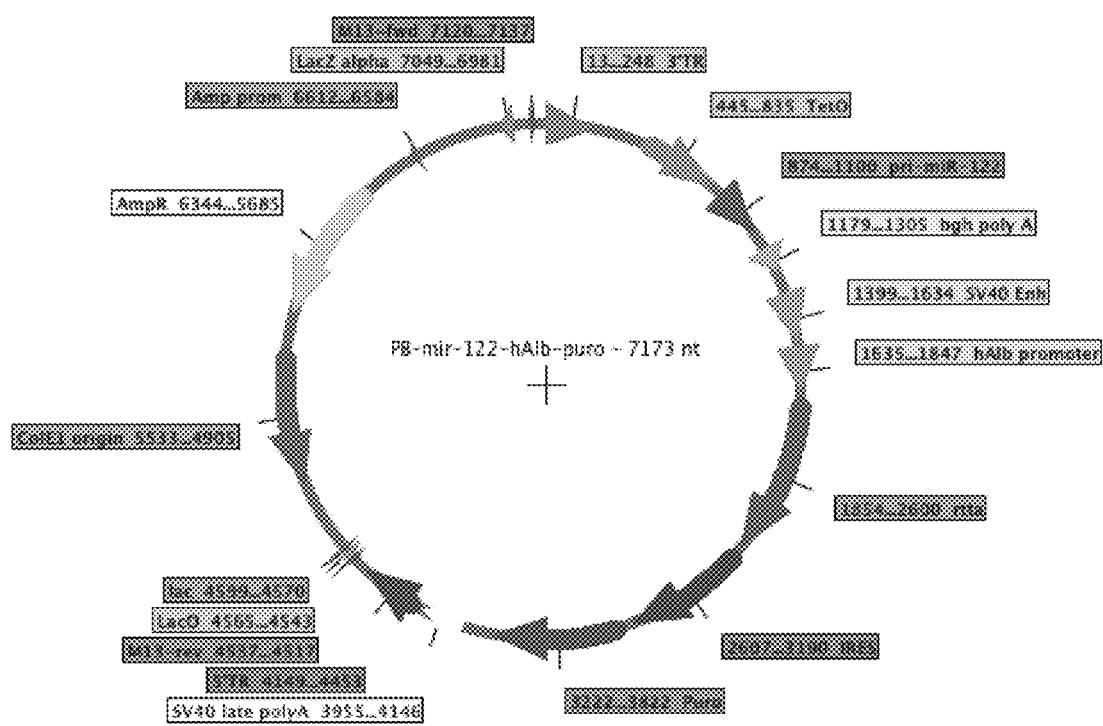
FIG. 7 is a schematic diagram showing a PiggyBac clone (pB-mir-122-hAlb-puro) carrying a puromycin resistance gene and an inducible mir-122 expression cassette.

A piggybac construct was made which had mir-122 under a tet inducible promoter and puromycin gene under a human albumin promoter (which would be active in hepatocytes). The vector map of the construct is shown in FIG. 7. The construct was electroporated into male human cryoplateable hepatocytes (Celsis, cat# M00995-P) and cells were selected with 1 ug/ml puromycin for 24 hours (in which time period all control non-electroporated cells died). Cells were maintained with hepatocyte growth medium (Promocell, cat# C25010) on Matrigel™ coated plates. 2 ug/ml doxycycline was used to induce mir-122 in transfected cells. Cells were collected on day 0 and on day 7 (both control and transfected cells). Gene expression was measured by QRT PCR and normalized by GAPDH.

Results.

The human primary hepatocytes transfected with the mir-122 microRNA expressing construct expressed 2.7-fold more miR-122 at day 7 as compared to normal hepatocytes (measured by Taqman QRT PCR for microRNAs, Applied Biosystems). At day 7, levels of functional enzymes in mir-122 expressing hepatocytes were greater than the levels of functional enzymes in untransfected hepatocytes (data not shown). This indicates that the forced overexpression of miRNA-122 using this alternative delivery method also elicits and maintains the expression of functional genes, as demonstrated in the previous Examples.

Example 5

Infection by and Replication of HBV in mir-122 Expressing Human Embryonic Stem Cell-Derived Hepatocytes In this example, we demonstrate that hepatitis B virus (HBV) can infect and successfully replicate in the hepatocytes produced from human embryonic stem cells according to the procedure outlined in Example 1.

Introduction.

Despite the availability of a vaccine against HBV, cirrhosis and liver cancer caused by HBV infection kill almost 1 million people worldwide/year. The infection and replication of HBV has not been previously reported in any non-transformed/non-immortalized cells other than in primary human hepatocytes. HBV also does not infect and grow in hepatocytes derived from other species. It also does not efficiently infect common human liver cancer derived cell lines such as Huh7 and HepG2. The only cancer cell line that HBV has been shown to infect and grow in is HepaRG (see Gripon et al., PNAS 2002, 99(24)). Although some cell lines may allow viral replication from viral genomes transfected via plasmid constructs, they do not allow replication via infection. Hence, there is a need in the art for a normal cell line that is infectable as well as which supports replication of the virus. Such a cell line would allow in vitro study of the complete viral life cycle, particularly its entry.

It would facilitate the identification of cellular receptors of HBV, development of anti-viral agents, and also would aid development of humanized mouse models to study innate immune response to viral infection, development of cirrhosis and finally cancer. It is very challenging to study the above in primary human hepatocytes because these cells apart from being are hard to obtain and costly, are extremely variable among batches isolated from different individuals. Moreover, primary hepatocytes de-differentiate in culture in a very short time thus changing in nature and introducing another level of variation. Lastly, since primary human hepatocytes do not grow in culture, contaminating fibroblasts, if present, rapidly take over the culture.

Methods.

Infectious HBV was produced using HepAD38 cells (Ladner et al, 1997, Antimicrobial agents and chemotherapy, 41(8)). Mir-122 transduced human embryonic stem cell-derived hepatocytes produced according to the method described in Example 1 above were then infected with the infectious HBV. Human primary hepatocytes were also infected with HBV to function as a positive control, and HepG2 cells were used as a negative control.

Infected cells were lysed at 6 days post-infection and treated with micrococcal nuclease. The viral capsule was broken with pronase and the viral DNA was isolated. QPCR was performed to quantify the viral genomes present in the isolated DNA using the QPCR primers disclosed by Watanabe et al. (PNAS 2007 104 (24)). The QPCR standard curve was prepared by serial dilution of LJ144, a construct that contains the whole viral genome.

Results.

Figure 8:
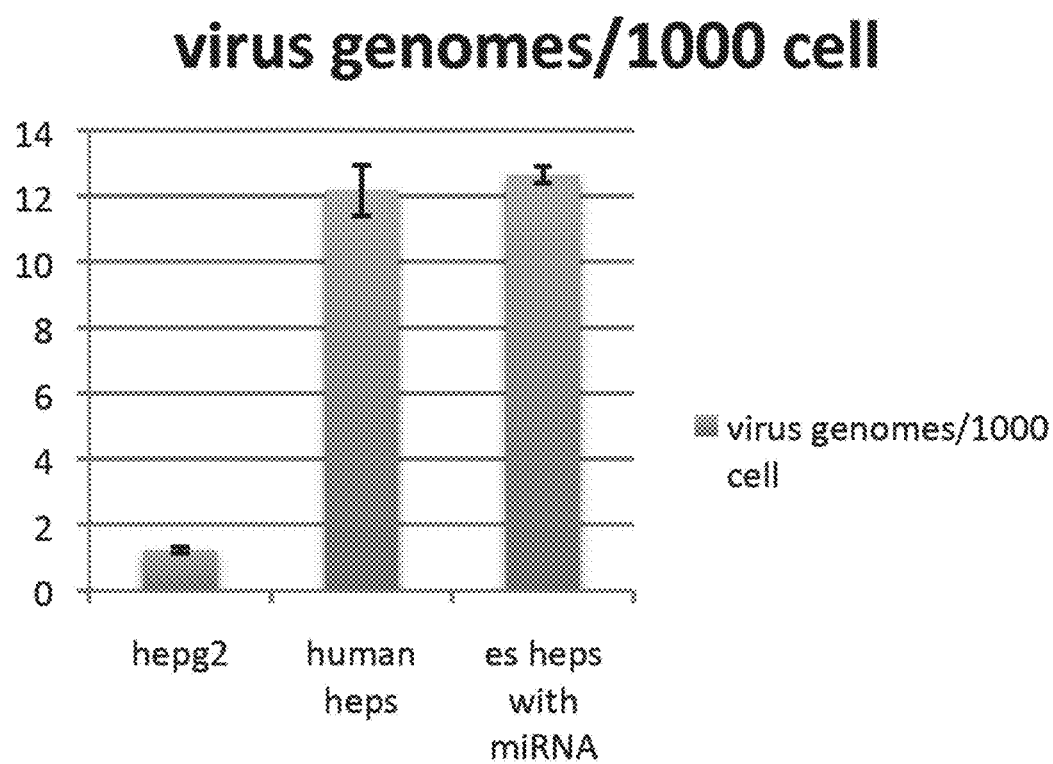
FIG. 8 is a bar graph showing that HBV infects and replicates in human embryonic stem cell-derived hepatocytes. Number of copies of the HBV genome is reported for human embryonic stem cell-derived hepatocytes transduced with mir-122 infected with HBV (es heps with miRNA), positive control (human heps), and negative controls (hepg2). The copy numbers were calculated by QPCR. QPCR standard curve was prepared by serial dilution of LJ144, a construct that contains the whole viral genome. Both LJ144 and QPCR primers were disclosed by Watanabe et al. (PNAS 2007 104 (24)).

FIG. 8 shows the number of viral genomes present per well in each cell type. The results clearly show the presence of HBV genomes in the mir-122 transduced human embryonic stem cell-derived hepatocytes (es heps with miRNA) and in the positive controls (human heps). In contrast, very little HBV was detected in the negative controls (hepg2).

These results demonstrate the successful infection and replication of HBV in the mature hepatocytes produced using the disclosed method, illustrating the usefulness of these cells in the study of HBV and potential anti-viral agents for use against HBV.

Example 6

Mir-122 Expression is Correlated with the Differentiation Status of Hepatocellular Carcinoma Cells In this example, we demonstrate that mir-122 expression levels in hepatocellular carcinoma tissue samples are strongly and positively correlated with the degree of differentiation exhibited by the cells within the tissue sample. Thus, mir-122 itself may be therapeutically useful for converting undifferentiated, highly malignant liver tumors into differentiated, less malignant ones.

Introduction.

Hepatocellular carcinoma (HCC) is the most common form of liver cancer. Most HCCs initially arise as highly differentiated tumors that are not very malignant. As the HCC further develops, the tumor is progressively de-differentiated and becomes increasingly malignant. Thus, there is a need for therapeutic agents that can help maintain a more highly differentiated, and thus less malignant, form of HCC.

Methods.

HCC tissue samples from 19 deceased patients were obtained from the Pathology Department at the University of Wisconsin—Madison Hospital. Notably, a single HCC tissue sample may have varying types of cells, from normal regions to regions having differentiated cancer cells to regions having poorly differentiated cancer cells. Accordingly, the HCC tumor tissue samples were analyzed by our collaborating pathologist, who identified various regions of the tumors in terms of their differentiation status. In the initial 19 tumor samples, the pathologist identified and classified a total of 31 tissue regions having different grades of differentiation. The pathologist classified each of these 31 tissue regions as normal, very well differentiated, well-moderately differentiated, moderately differentiated, moderate-poorly differentiated, or poorly differentiated.

The 31 tissue regions that were classified by differentiation state were then harvested by laser-microdissection. RNA was isolated from each of the harvested tissue regions, and RNA expression levels for both mir-122 and U6 snoRNA were measured using quantitative PCR. Mir-122 expression was normalized relative to U6 snoRNA expression.

Results.

Figure 9:
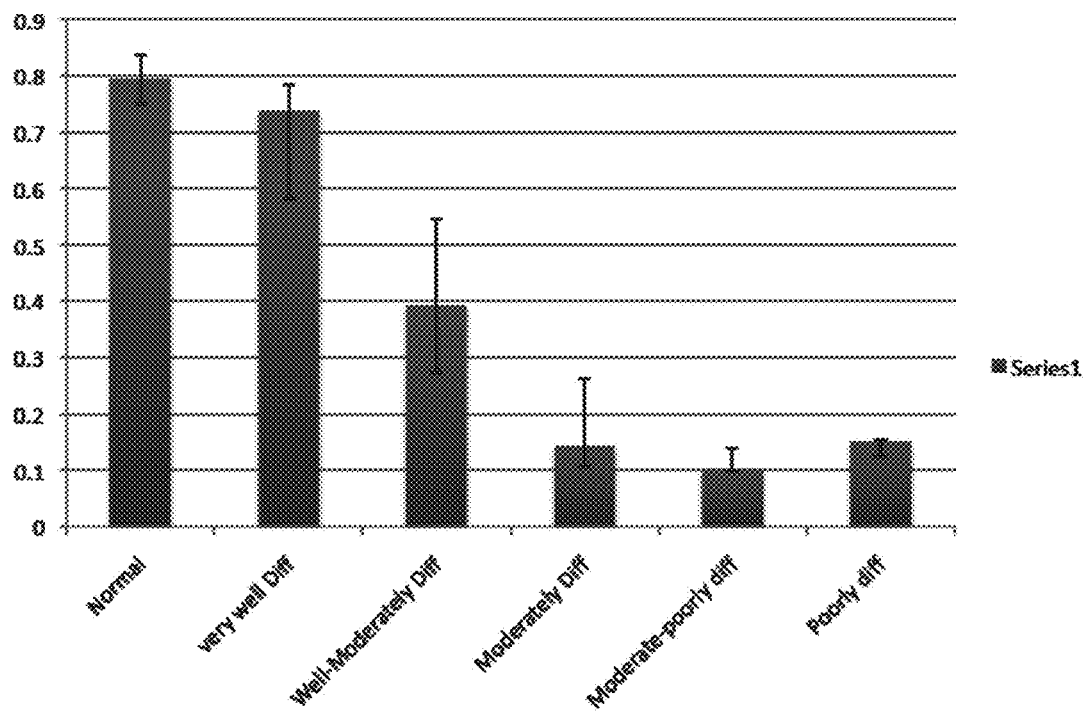
FIG. 9 is a bar graph showing that expression levels of mir-122 in human hepatocellular carcinoma tissue are correlated with the differentiation status of the carcinoma. Human hepatocellular carcinoma tissue samples were obtained from nineteen deceased patients. A total of 31 tissue regions having varying grades of cellular differentiation (as indicated along the X-axis for the six different bars) were harvested by laser-microdissection. Using quantitative PCR, expression of both mir-122 and U6 snoRNA was measured in each tissue region. Mir-122 expression levels shown along the Y axis are normalized by U6 snoRNA expression (RQ or relative quantity values, error bars representing standard error, RQ min and RQ max).

FIG. 9 shows normalized mir-122 expression as a function of decreasing degree of HCC tissue differentiation. The results show a clear positive correlation between mir-122 expression levels and degree of HCC tissue differentiation. Taken together with the data reported above, this Example demonstrates the potential of managing HCC by administering the microRNA mir-122 to a patient with HCC to maintain the differentiated status of the HCC, thus decreasing the potential malignancy of the HCC.

Example 7

Let-7c Expression in Human Embryonic Stem Cell-Derived Hepatocytes, Alone and/or in Combination with mir-122 Expression, Substantially Up-Regulates Cytochrome P450 and Other Liver Genes, Substantially Down-Regulates Alpha-Feto Protein, Facilitates Highly Efficient Drug Processing, and Inhibits Replication of HBV Summary In this example, we demonstrate that the expression of another miRNA, let-7c, can be used to up-regulate mature hepatic genes in hESC-derived hepatocytes. Furthermore, let-7c expressing hESC-derived hepatocytes exhibit substantial down-regulation of alpha-feto protein, a widely recognized marker for fetal tissue. Alpha-feto protein was not down-regulated in the previous examples using mir-122 expressing hESC-derived hepatocytes.

Increased let-7c expression, without a concurrent increase in mir-122 expression, did not elicit induction of the corresponding cytochrome P450 genes when the hESC-derived hepatocytes were challenged with omeprazole and rifampicin (and in fact, these genes were down-regulated). However when we transduced the hESC-derived hepatocytes with both mir-122 and let-7c, the corresponding cytochrome P450 genes were strongly induced upon challenge with omeprazole and rifampicin. This demonstrates the potential usefulness of hESC-derived hepatocytes expressing both mir-122 and let-7c in drug metabolism and toxicity testing.

Furthermore, we demonstrate that let-7c expression significantly down-regulated productive infection of the hESC-derived hepatocytes by hepatitis B virus (HBV). This demonstrates the potential therapeutic value of the let-7c expressing hESC-derived hepatocytes in the treatment of HBV and HCV associated liver diseases, such as cirrhosis and liver cancer.

Results

In the previous examples, we had shown the successful up-regulation of hepatic genes by transducing a liver-specific miRNA, hsa-mir-122, into our hESC-derived hepatocytes. In this example, we demonstrate that transduction of hsa-let-7c, both alone and in combination with hsa-mir-122, can also up-regulate expression of functional and mature genes in ES derived hepatocytes.

Figure 10:
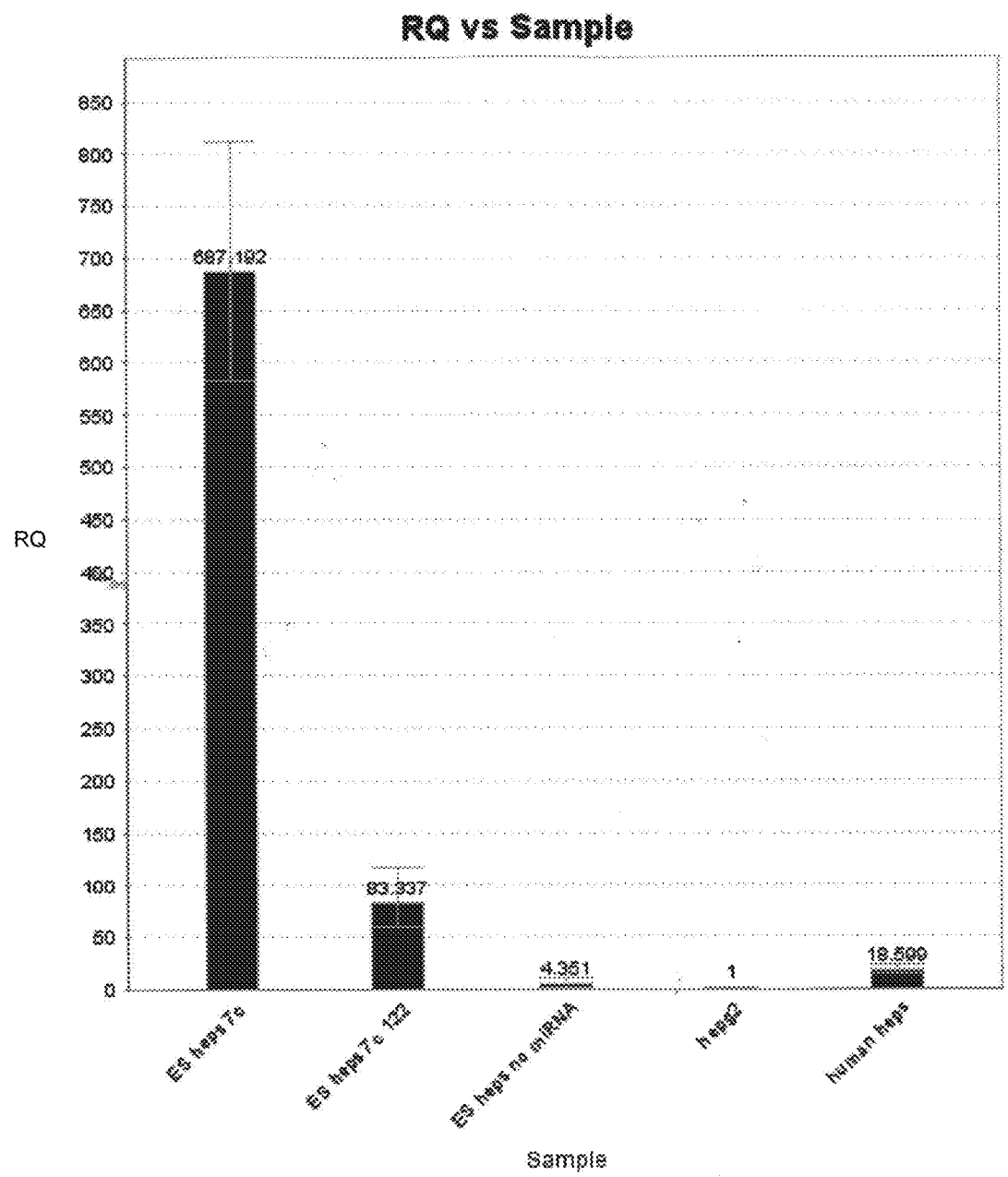
FIG. 10 is a bar graph comparing expression levels for the protein albumin in non-transduced hESC derived hepatocytes (ES heps no miRNA), hESC derived hepatocytes transduced with let-7c (ES heps 7c), hESC derived hepatocytes transduced with both let-7c and mir-122 (ES heps 7c 122), and conventionally derived human hepatocytes (human heps). Expression of albumin was also measured in HepG2, a human hepatoma cell line (hepg2). Expression was measured by quantitative PCR. Indicated expression levels (on the Y axis) are GAPDH normalized gene expression values called RQ values (relative quantity values), with HepG2 expression assigned a relative value of 1. Error bars indicate RQ min and RQ max values calculated on 1 standard deviation. All RQ, RQ min and RQ max values were calculated with ViiA7 software on Applied Biosystems QPCR system.
Figure 11:
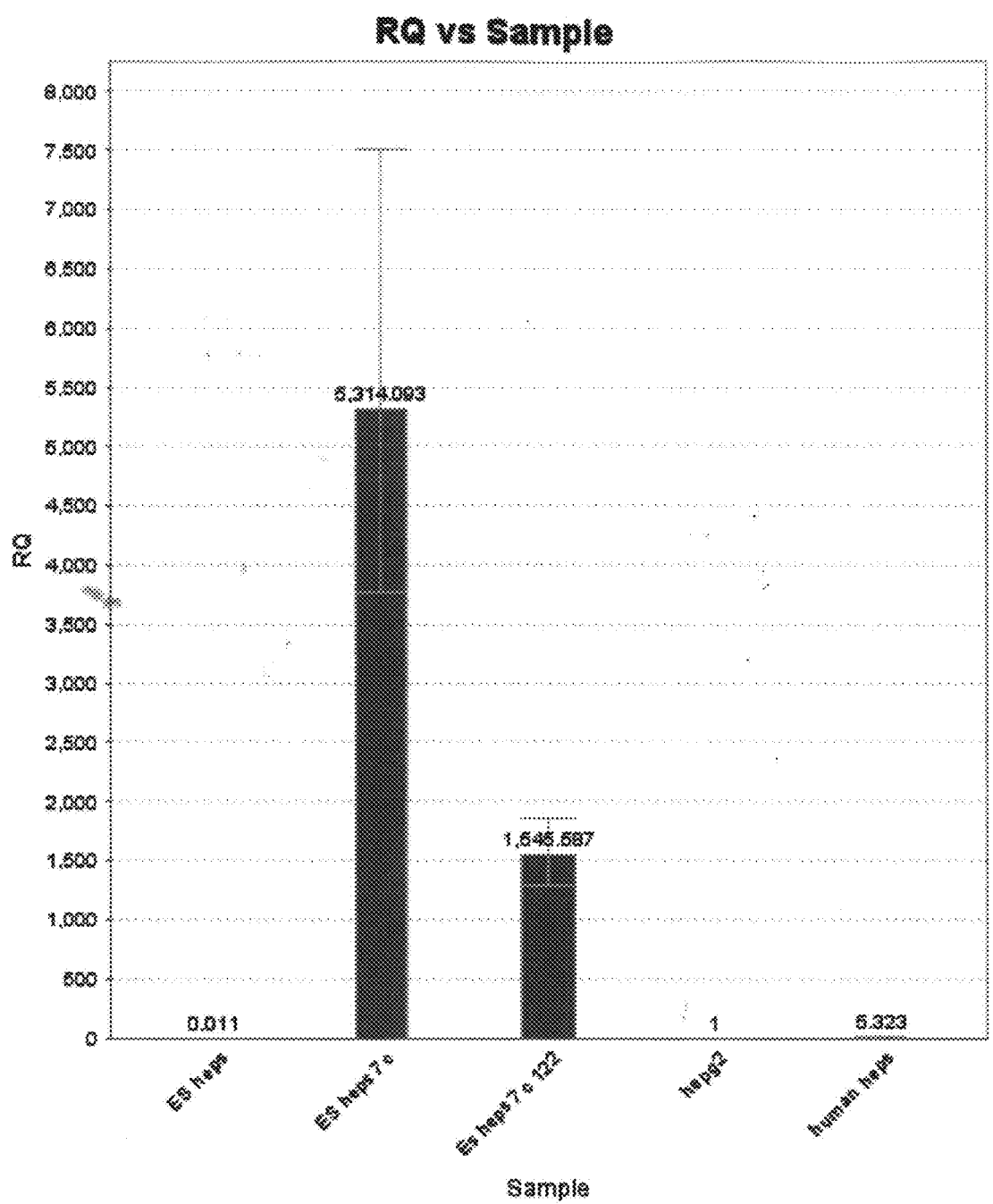
FIG. 11 is a bar graph comparing expression levels for the CYP P450 enzyme CYP7A1 in non-transduced hESC derived hepatocytes (ES heps), hESC derived hepatocytes transduced with let-7c (ES heps 7c), hESC derived hepatocytes transduced with both let-7c and mir-122 (ES heps 7c 122), and conventionally derived human hepatocytes (human heps). Expression of CYP7A1 was also measured in HepG2, a human hepatoma cell line (hepg2). Expression was measured by quantitative PCR. Indicated expression levels (on the Y axis) are GAPDH normalized gene expression values called RQ values (relative quantity values), with HepG2 expression assigned a relative value of 1. Error bars indicate RQ min and RQ max values calculated on 1 standard deviation. All RQ, RQ min and RQ max values were calculated with ViiA7 software on Applied Biosystems QPCR system.
Figure 12:
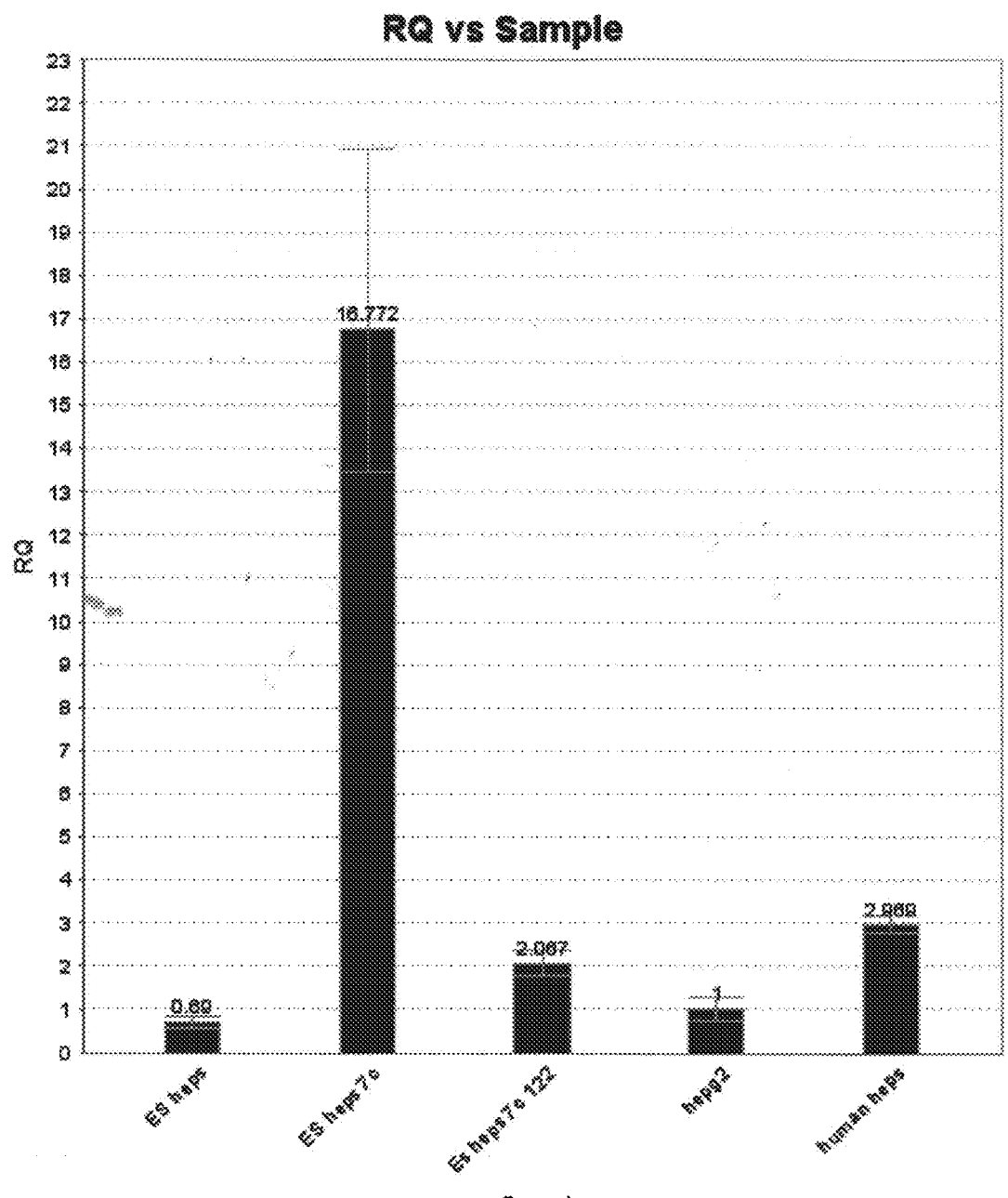
FIG. 12 is a bar graph comparing expression levels for the CYP P450 enzyme CYP3A4 in non-transduced hESC derived hepatocytes (ES heps), hESC derived hepatocytes transduced with let-7c (ES heps 7c), hESC derived hepatocytes transduced with both let-7c and mir-122 (ES heps 7c 122), and conventionally derived human hepatocytes (human heps). Expression of CYP3A4 was also measured in HepG2, a human hepatoma cell line (hepg2). Expression was measured by quantitative PCR. Indicated expression levels (on the Y axis) are GAPDH normalized gene expression values called RQ values (relative quantity values), with HepG2 expression assigned a relative value of 1. Error bars indicate RQ min and RQ max values calculated on 1 standard deviation. All RQ, RQ min and RQ max values were calculated with ViiA7 software on Applied Biosystems QPCR system.
Figure 13:
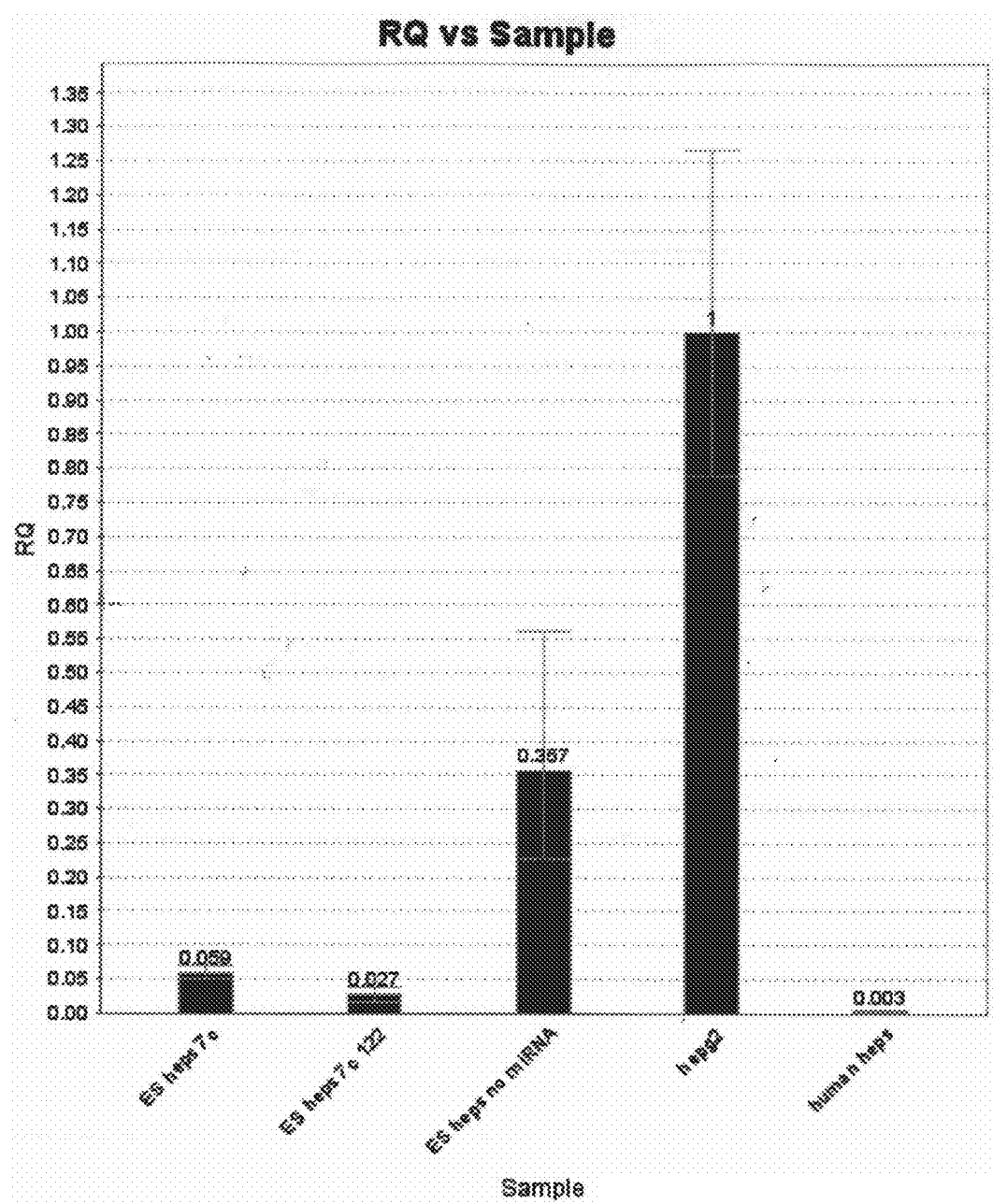
FIG. 13 is a bar graph comparing expression levels for the fetal marker alpha-feto protein (AFP) in non-transduced hESC derived hepatocytes (ES heps no miRNA), hESC derived hepatocytes transduced with let-7c (ES heps 7c), hESC derived hepatocytes transduced with both let-7c and mir-122 (ES heps 7c 122), and conventionally derived human hepatocytes (human heps). Expression of AFP was also measured in HepG2, a human hepatoma cell line (hepg2). Expression was measured by quantitative PCR. Indicated expression levels (on the Y axis) are GAPDH normalized gene expression values called RQ values (relative quantity values), with HepG2 expression assigned a relative value of 1. Error bars indicate RQ min and RQ max values calculated on 1 standard deviation. All RQ, RQ min and RQ max values were calculated with ViiA7 software on Applied Biosystems QPCR system.
Figure 14:
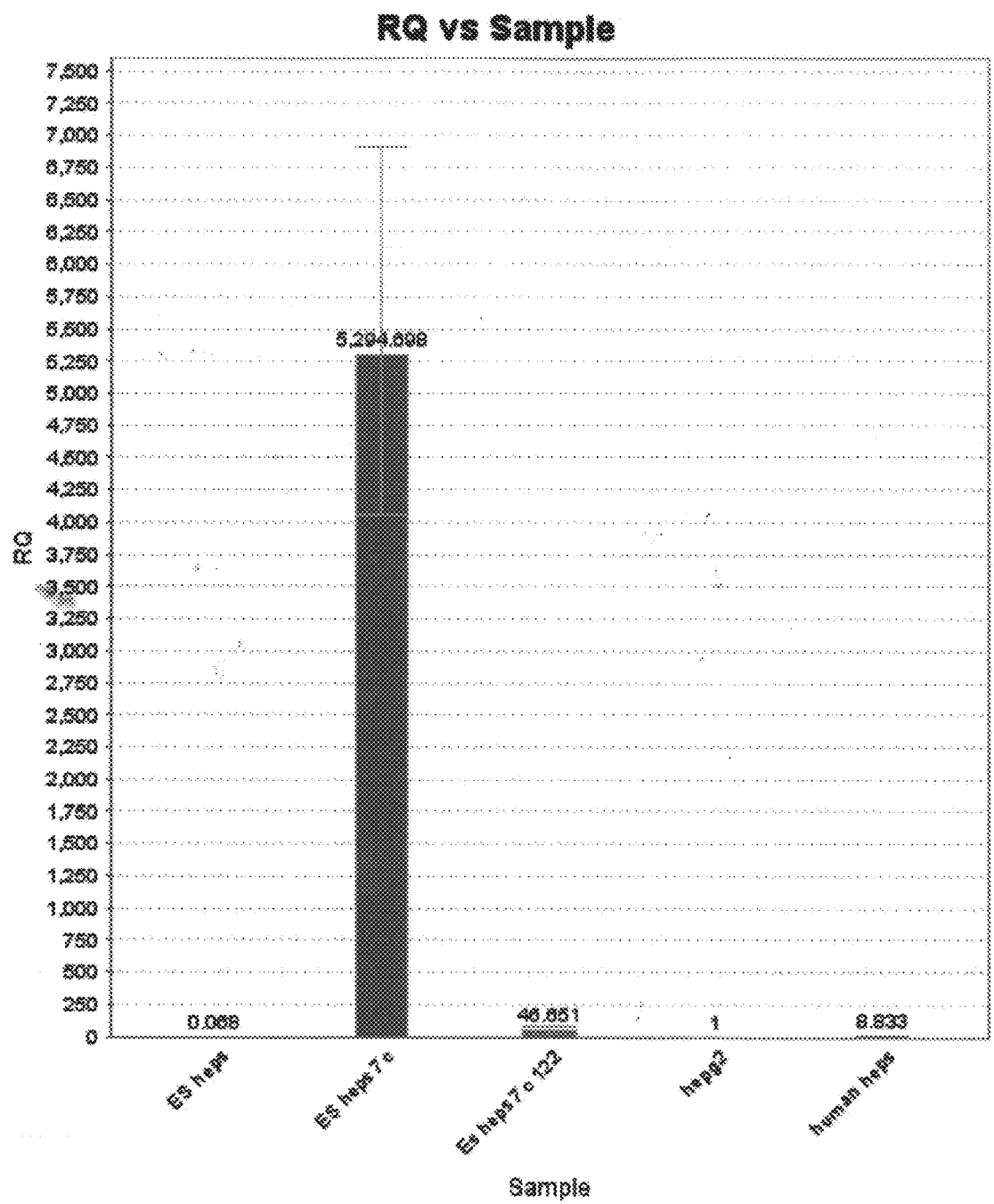
FIG. 14 is a bar graph comparing expression levels for the CYP P450 enzyme CYP1A2 in non-transduced hESC derived hepatocytes (ES heps), hESC derived hepatocytes transduced with let-7c (ES heps 7c), hESC derived hepatocytes transduced with both let-7c and mir-122 (ES heps 7c 122), and conventionally derived human hepatocytes (human heps). Expression of AFP was also measured in HepG2, a human hepatoma cell line (hepg2). Expression was measured by quantitative PCR. Indicated expression levels (on the Y axis) are GAPDH normalized gene expression values called RQ values (relative quantity values), with HepG2 expression assigned a relative value of 1. Error bars indicate RQ min and RQ max values calculated on 1 standard deviation. All RQ, RQ min and RQ max values were calculated with ViiA7 software on Applied Biosystems QPCR system.

We transduced our hESC derived hepatocytes as described in the previous examples (see methods below) to express either let-7c alone or let-7c along with mir-122. Mature hepatocyte specific genes, including albumin (FIG. 10), CYP7A1 (FIG. 11), CYP3A4 (FIG. 12) and CYP1A2 (FIG. 14) were up-regulated in cells expressing let-7c. Interestingly, the fetal marker AFP (alpha-feto protein) was down-regulated by let-7c expression, which indicates that let-7c facilitates maturing of the hepatocytes (FIG. 13).

In the same figures it can also be seen that cells expressing both let-7c and mir-122 also show up-regulation of these hepatocyte specific genes, although to a lesser extent than let-7c alone (FIGS. 10, 11, 12 and 14). The expression of AFP is also down-regulated in cells expressing both miRNAs (FIG. 13).

Figure 15:
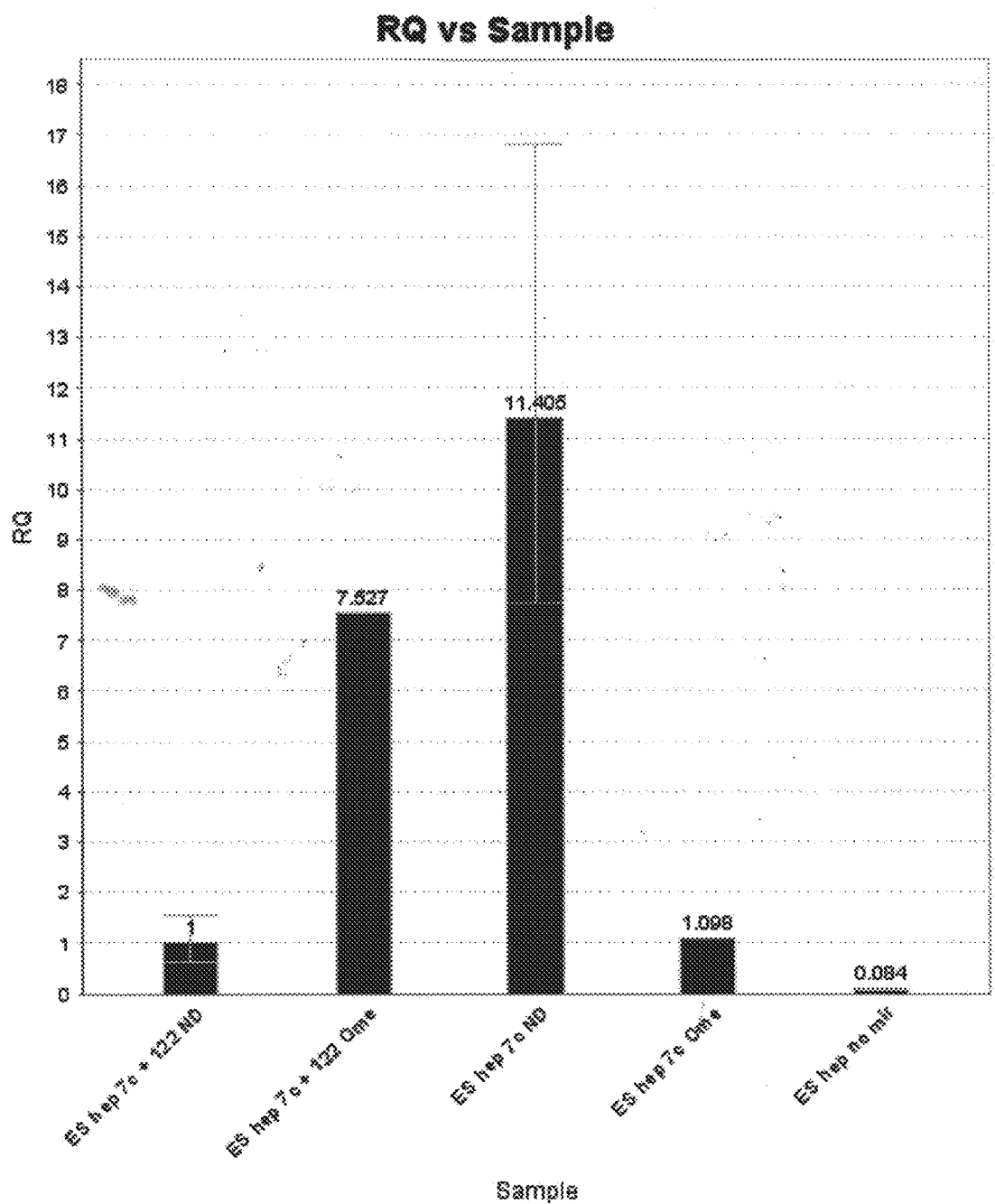
FIG. 15 is a bar graph comparing expression levels for the CYP P450 enzyme CYP1A2 in non-transduced hESC derived hepatocytes (ES hep no mir), hESC derived hepatocytes transduced with let-7c with no drug challenge (ES hep7cND), hESC derived hepatocytes transduced with let-7c challenged with omeprazole (EShep7c Ome), hESC derived hepatocytes transduced with both let-7c and mir-122 with no drug challenge (ES hep7c+122ND), and hESC derived hepatocytes transduced with both let-7c and mir-122 challenged with omeprazole (EShep7c+122Ome). The graph shows that embryonic stem cell derived hepatocytes expressing both mir-122 and let-7c exhibit substantial induction of CYP1A2 by omeprazole. Expression was measured by quantitative PCR, and the expression levels are shown as GAPDH normalized gene expression values, with expression of the hESC derived hepatocytes transduced with both let-7c and mir-122 with no drug challenge assigned a relative value of 1. (RQ values or relative quantity values. Error bars indicate RQ min and RQ max values).
Figure 16:
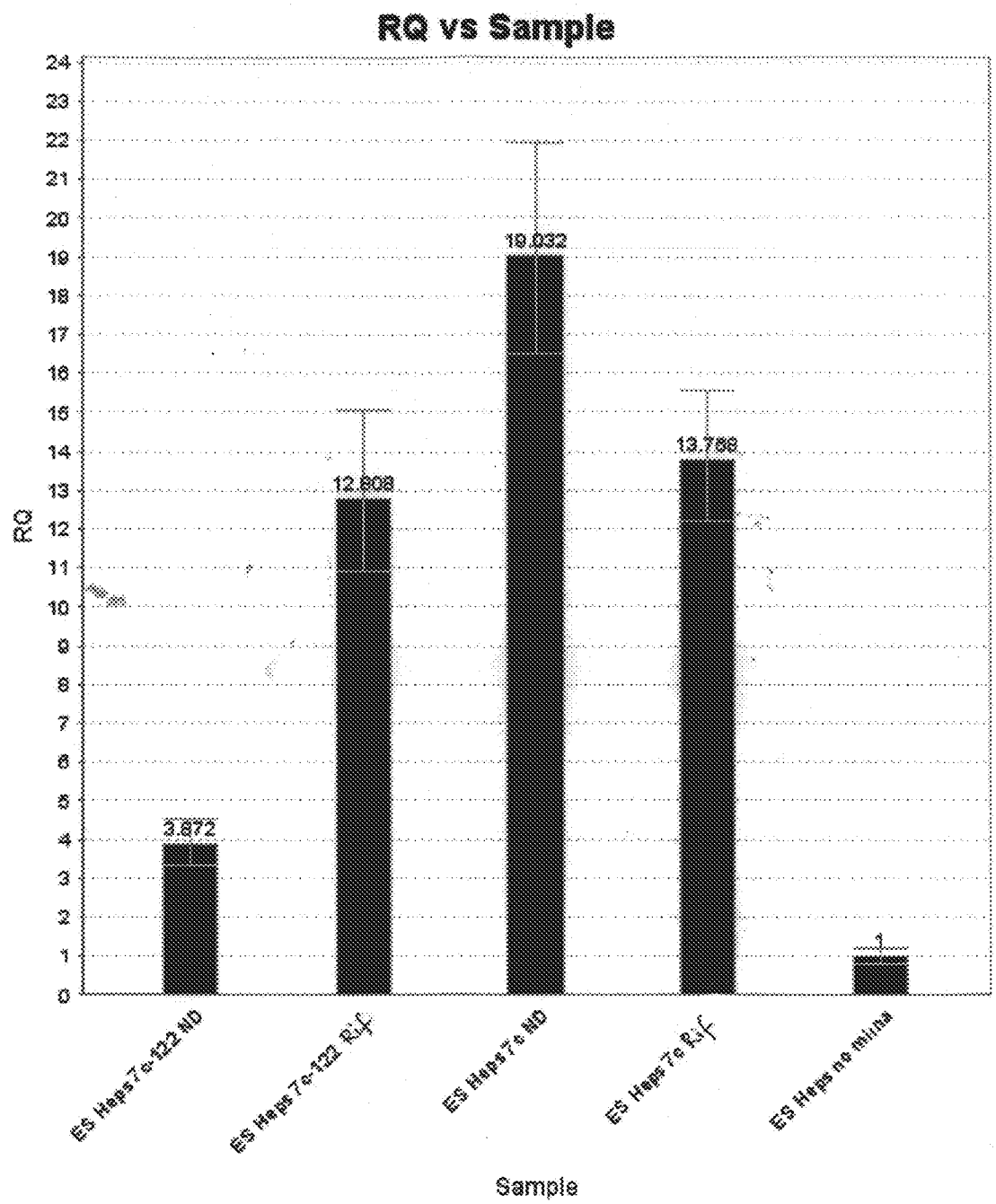
FIG. 16 is a bar graph comparing expression levels for the CYP P450 enzyme CYP3A4 in non-transduced hESC derived hepatocytes (ES Heps no mirna), hESC derived hepatocytes transduced with let-7c with no drug challenge (ES Heps7c ND), hESC derived hepatocytes transduced with let-7c challenged with rifampin (ES Heps7c Rif), hESC derived hepatocytes transduced with both let-7c and mir-122 with no drug challenge (ES Heps7c-122 ND), and hESC derived hepatocytes transduced with both let-7c and mir-122 challenged with rifampin (ES Heps7c-122 Rif). The graph shows that embryonic stem cell derived hepatocytes expressing both mir-122 and let-7c exhibit substantial induction of CYP3A4 by rifampin. Expression was measured by quantitative PCR, and the expression levels are shown as GAPDH normalized gene expression values, with expression of the non-transduced hESC derived hepatocytes assigned a relative value of 1. (RQ values or relative quantity values. Error bars indicate RQ min and RQ max values).

Although cytochrome P450 genes are up-regulated by the miRNA let-7c, another test of hepatocyte maturity is the ability to induce the appropriate cyp genes upon challenge by specific drugs. Both omeprazole (FIG. 15) and rifampin (FIG. 16) induced the expression of their respective cyp genes, namely, CYP1A2 and CYP3A4, in cells co-expressing both mir-122 and let-7c, as compared to non-drug treated (ND) cells. Interestingly, although let-7c up-regulates general expression of cyp genes, it alone is not sufficient to generate induction of cytochrome 450 genes through specific drug challenge.

Figure 17:
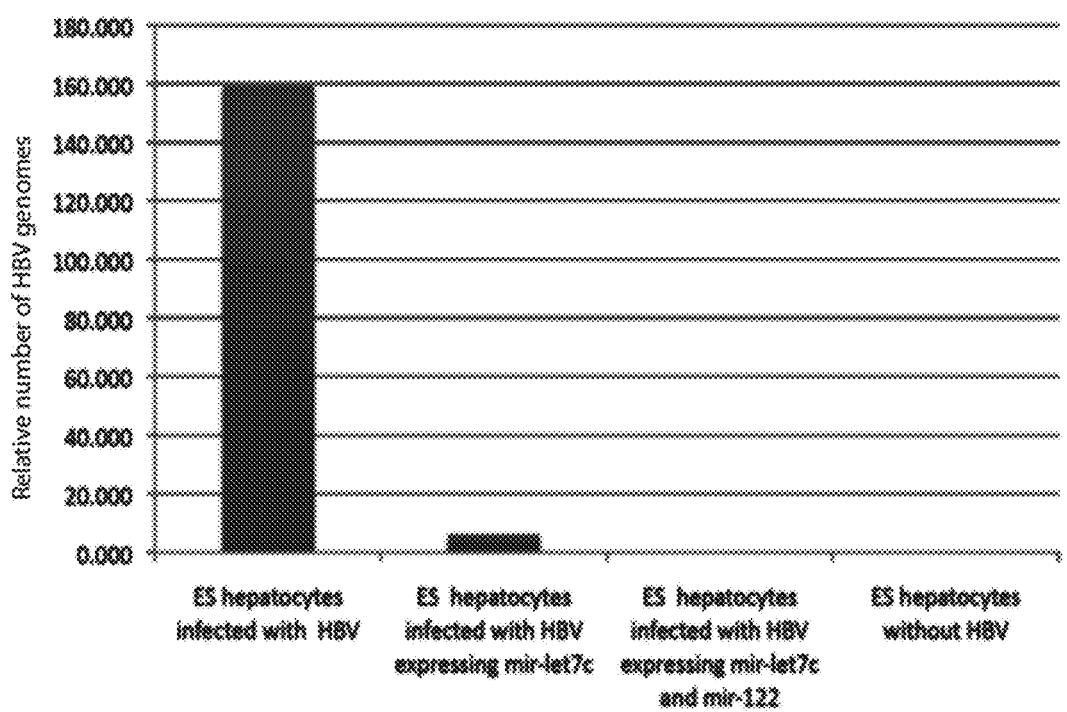
FIG. 17 is a bar graph reporting the relative number of copies of the HBV genome detected for non-transduced human embryonic stem cell-derived hepatocytes infected with HBV (ES hepatocytes infected with HBV), human embryonic stem cell-derived hepatocytes transduced with let-7c infected with HBV (ES hepatocytes infected with HBV expressing mir-let-7c), human embryonic stem cell-derived hepatocytes transduced with both let-7c and mir-122 infected with HBV (ES hepatocytes infected with HBV expressing mir-let-7c and mir-122), and negative controls (ES hepatocytes without HBV). The copy numbers were calculated by QPCR. QPCR standard curve was prepared by serial dilution of LJ144, a construct that contains the whole viral genome. Both LJ144 and QPCR primers were disclosed by Watanabe et al. (PNAS 2007 104 (24)).

Finally, we measured the relative number of copies of the HBV genome detected for non-transduced human embryonic stem cell-derived hepatocytes infected with HBV, human embryonic stem cell-derived hepatocytes transduced with let-7c infected with HBV, human embryonic stem cell-derived hepatocytes transduced with both let-7c and mir-122 infected with HBV, and negative controls (FIG. 17). Let-7c expression significantly down-regulated productive infection of the hESC-derived hepatocytes by HBV, while co-expression of both let-7c and mir-122 further down-regulated productive infection.

Materials and Methods

HBV Infection.

Infectious HBV virions were concentrated from media of HepAD38 cells (Ladner et al. 1997) by PEG 8000 precipitation followed by centrifugation. These virions were used to infect let-7c transduced hESC derived hepatocytes, let-7c and mir-122 transduced hESC derived hepatocytes, and control (untransduced) hESC derived hepatocytes. Inoculum was removed after 24 hours and cells were washed thoroughly. On the seventh day after infection, the cells were lysed in a buffer containing NP49, nuclei were pelleted, and the lysates were treated with micrococcal nuclease followed by pronase. Viral nucleic acids were then isolated by phenol:chloroform extraction. Viral genome copy numbers were quantified by QPCR using primers previously published (see Watanabe et al. 2007). Standard curve for QPCR was generated by serial dilution of LJ144, a construct that contains the whole viral genome (see Watanabe et al. 2007).

Lentiviral miRNA Expression.

Mir-122 and let-7c were transduced into the hESC derived hepatocytes on day 8 of differentiation by a lentiviral vector pEZX-MR03 (Genecoepoeia). GFP expressing transduced cells were FACS sorted for mRNA profiling by QPCR using Sybr green.

Hepatocyte Differentiation.

H1 ES cells cultured in E8 media (Chen et al. 2011) were differentiated to hepatocytes following a previously published protocol (Cai et al. 2007) with some modifications. Briefly, at approximately 50% confluency the ES cells were treated with 0.5 mg/ml Albumin fraction V (Sigma) and 100 ng/ml Activin A (Sigma) for three days. During the second and third days 0.1% and 1.0% Insulin-transferrin-Selenium (Sigma) were added respectively. From day 4 to day 8 the cells were treated with 30 ng/ml FGF4 (R&D Systems) along with 20 ng/ml BMP2. Days 9 through 13, 20 ng/ml HGF (R&D Systems) were added to the media, and finally the cells were treated for five days with 10 ng/ml Oncostatin M (R&D Systems) and 0.1 µM Dexamethasone (Sigma). Throughout differentiation, hepatocyte growth media (Promocell) were used and cells were kept on matrigel-coated plates. Cells were transduced with mir-122 and let-7c on day 8.

TABLE 1

Sequences of QPCR primers used in this study.

| | |
|---|---|
| GAPDH forward | TCAACGACCACTTTGTCAAGCT (SEQ ID NO: 9) |
| GAPDH reverse | CCATGAGGTCCACCACCCT (SEQ ID NO: 10) |
| ALB forward | CAAAGATGTGTTGCTATCCTGAAAA (SEQ ID NO: 11) |
| ALB reverse | CCGAAGTGGAATAAGAGAGAACACT (SEQ ID NO: 12) |
| AFP forward | CTTGAGGCTGTCATTGCAGATT (SEQ ID NO: 13) |
| AFP reverse | CCTGGCCTTGGCAGCAT (SEQ ID NO: 14) |
| CYP1A2 forward | GCCCGGCCCACAATTAA (SEQ ID NO: 15) |
| CYP1A2 reverse | GCTAATGGGTGCAGGGTTTC (SEQ ID NO: 16) |
| CYP3A4 forward | GGCAGGAGAATCACTTGAACCT (SEQ ID NO: 17) |
| CYP3A4 reverse | GAGTGCAGTGGTGCAATCTCA (SEQ ID NO: 18) |
| CYP7A1 forward | GGAGTGTATTAAGTGCAGCTTGACA (SEQ ID NO: 19) |
| CYP7A1 reverse | CACCTTAGTTTTTTTCATCTGCAA (SEQ ID NO: 20) |
| HBV forward* | CCTATGGGAGTGGGCCTCA (SEQ ID NO: 21) |
| HBV reverse* | CCCCAATACCACATCATCCATATA (SEQ ID NO: 22) |

*from Watanabe et al

REFERENCES

Chen, G., Gulbranson, D. R., Hou, Z., Bolin, J. M., Ruotti, V., Probasco, M. D., Smuga-Otto, K., Howden, S. E., Diol, N. R., Propson, N. E., et al. (2011). Nat. Methods 8, 424-429.

Cai, J., Zhao, Y., Liu, Y., Ye, F., Song, Z., Qin, H., Meng, S., Chen, Y., Zhou, R., Song, X., et al. (2007). Hepatology 45, 1229-1239.

Watanabe, T., Sorensen, E. M., Naito, A., Schott, M., Kim, S., and Ahlquist, P. (2007) Proc. Natl. Acad. Sci. USA. 104, 10205-10210.

Example 8

Let-7c Expression is Correlated with the Differentiation Status of Hepatocellular Carcinoma Cells In this example, we demonstrate that let-7c expression levels in hepatocellular carcinoma tissue samples are strongly and positively correlated with the degree of differentiation exhibited by the cells within the tissue sample. Thus, let-7c itself may be therapeutically useful for converting undifferentiated, highly malignant liver tumors into differentiated, less malignant ones.

We next looked at expression of let-7c in human liver cancer samples using the procedures outlined in Example 6 above for mir-122 expression. We found that, as with mir-122 expression, let-7c expression is associated with the differentiation status of liver cancer.

Results.

Figure 18:
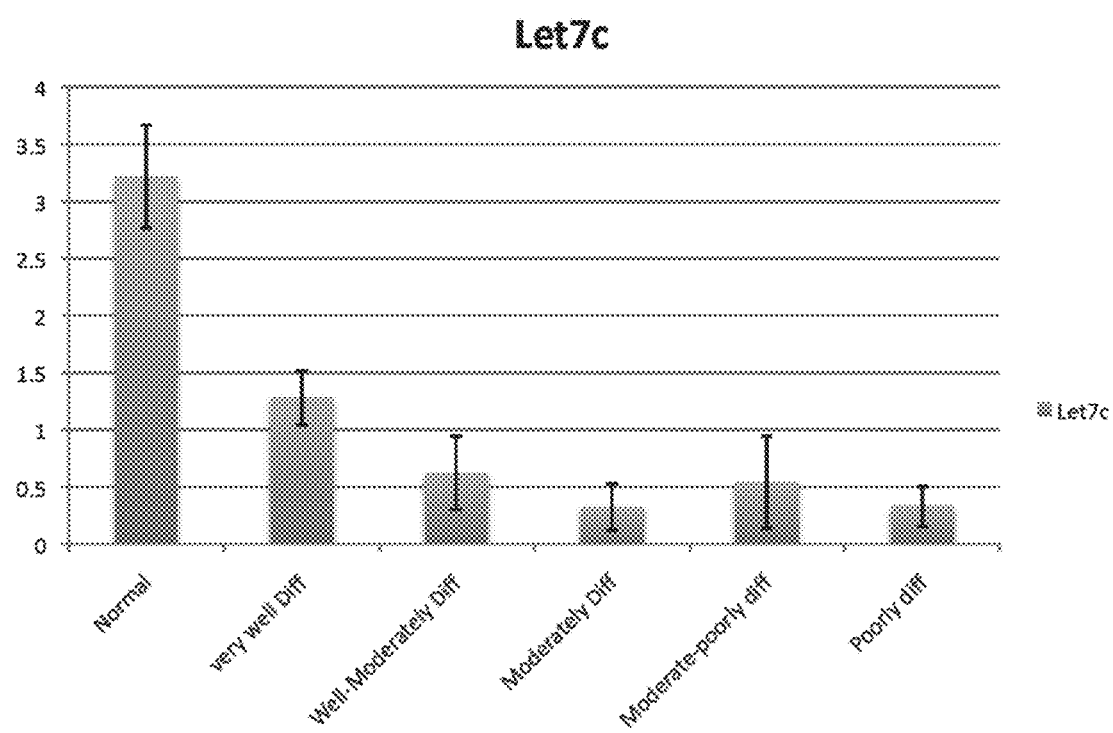
FIG. 18 is a bar graph showing that expression levels of let-7c in human hepatocellular carcinoma tissue is correlated with the differentiation status of the carcinoma. Using quantitative PCR, expression of both let-7c and U6 snoRNA was measured in a number of regions of human hepatocellular carcinoma tissue samples from deceased patients. Let-7c expression levels shown along the Y axis are normalized by U6 snoRNA expression (RQ or relative quantity values, error bars representing standard error, RQ min and RQ max).

FIG. 18 shows normalized let-7c expression as a function of decreasing degree of HCC tissue differentiation. The results show a clear positive correlation between let-7c expression levels and degree of HCC tissue differentiation. This example demonstrates the potential of managing HCC by administering the microRNA let-7c to a patient with HCC to maintain the differentiated status of the HCC, thus decreasing the potential malignancy of the HCC.

Example 9

Expressing microRNA Having the Functionality of miR-122 and/or miR-let-7c

In this prophetic example, we suggest that in any of the previous examples wherein miR-122 and/or miR-let-7c is expressed, similar results would have been obtained by expressing a miRNA having the functionality of miR-122 and/or miR-let-7c. In order to "have the functionality" of miR-122, the microRNA must have a core sequence that is 18-24 nucleotides long. In addition, the core sequence must contain, within its 10-nucleotide 5' end, a seed sequence that consists of any 6, 7, 8, 9 or 10 consecutive nucleotides of the 10-nucleotide 5' end of the miR-122 sequence (SEQ ID NO:5). Given this guidance, the skilled artisan could readily use known methods to make or express a variety of miRNAs having the required functionality.

In order to "have the functionality" of miR-let-7c, the microRNA must have a core sequence that is 18-24 nucleotides long. In addition, the core sequence must contain, within its 10-nucleotide 5' end, a seed sequence that consists of any 6, 7, 8, 9 or 10 consecutive nucleotides of the 10-nucleotide 5' end of the let-7c family (SEQ ID NO:6, SEQ ID NO:7, or SEQ ID NO:8). Once again, given this guidance, the skilled artisan could readily use known methods to make or express a variety of miRNAs having the required functionality.

Example 10

Drug Metabolism Testing Using Human Embryonic Stem Cell-Derived Hepatocytes

In this example, we report the results of drug metabolism testing using our embryonic stem cell-derived hepatocytes. Specifically, we quantified the amount of the Rifampin metabolite 25-des acetyl rifampin produced upon incubation of various cell types with Rifampin. The cell types used, including non-transduced hESC derived hepatocytes, hESC derived hepatocytes transduced with let-7c, hESC derived hepatocytes transduced with mir-122, hESC derived hepatocytes transduced with both let-7c and mir-122, conventionally obtained human hepatoctyes, and a negative control (HepG2), were described in the previous examples.

Figure 19:
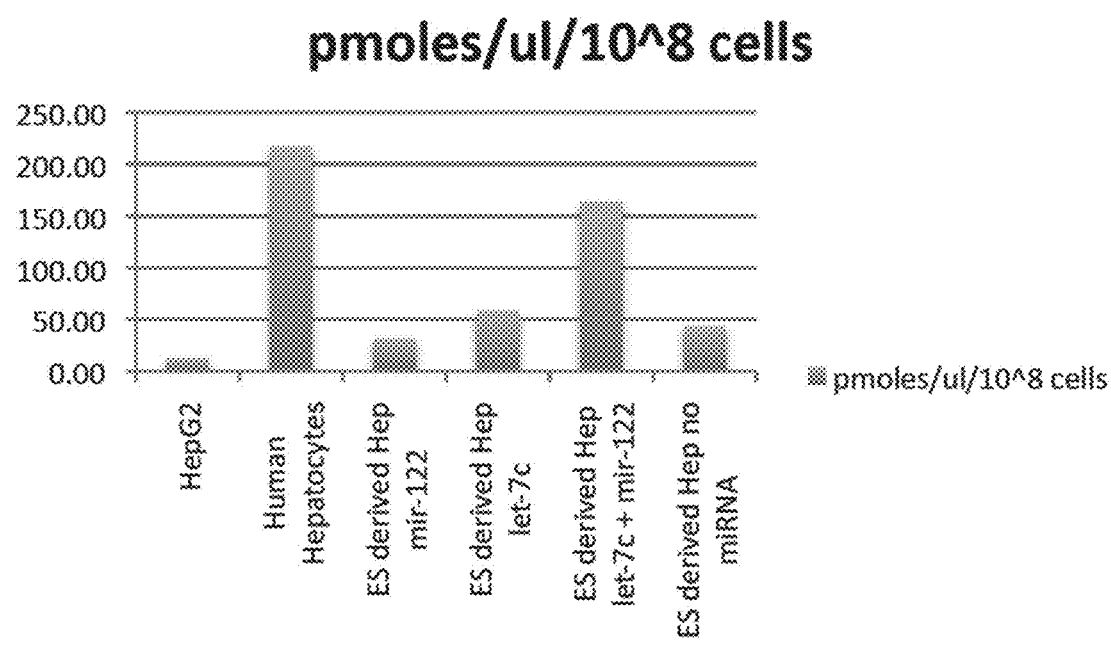
FIG. 19 is a bar graph showing that embryonic stem cell derived hepatocytes co-transduced with both mir-122 and let-7c are able to metabolize drugs with efficiency comparable to primary human hepatocytes. The bar graph compares the amount of the Rifampin metabolite 25-des acetyl rifampin produced (indicated on the Y axis in pmoles/ul/$10^8$ cells) upon incubation with Rifampin of the cell types indicated on the X axis. Metabolite was quantified using liquid chromatography with tandem mass spectrometry (LC-MS/MS). Cell types tested included non-transduced hESC derived hepatocytes (ES derived Hep no miRNA), hESC derived hepatocytes transduced with let-7c (ES derived Hep let-7c), hESC derived hepatocytes transduced with mir-122 (ES derived Hep mir-122), hESC derived hepatocytes transduced with both let-7c and mir-122 (ES derived Hep let-7c+mir-122), conventionally obtained human hepatoctyes, and a negative control (HepG2).

The cells were incubated with Rifampin for 72 hours, after which the media was collected and the metabolite of rifampin, 25-des acetyl rifampin, was measured by liquid chromatography and tandem mass spectrometry (LC-MS/MS). FIG. 19 shows the amount of 25-des acetyl rifampin produced by the various cells types. The results show that hESC derived hepatocytes co-transduced with both let-7c and mir-122 are able to metabolize Rifampin with efficiency comparable to primary human hepatocytes (see FIG. 19).

The invention is not limited to the embodiments set forth herein for illustration, but includes everything that is within the scope of the claims. Furthermore, all references cited herein are hereby incorporated by reference in their entirety and for all purposes as if fully set forth herein.

We claim:

1. A culture comprising one or more isolated mature hepatocytes, wherein after nine days of culture, at least one of the hepatocytes maintains expression levels of tyrosine aminotransferase (TAT) that is at least 80% of the level that was exhibited when the culture was established, wherein the cells are expressing an exogenous sequence comprising
   - (a) a first microRNA comprising a core sequence that is 18 to 24 nucleotides long, wherein the 10 nucleotide sequence on the 5' end of the core sequence comprises a seed sequence consisting of any 6, 7, 8, 9 or 10 consecutive nucleotides of SEQ ID NO:5; or
   - (b) an external vector comprising a DNA sequence coding for the first microRNA; or
   - (c) a second microRNA comprising a core sequence that is 18 to 24 nucleotides long; wherein the 10 nucleotide sequence on the 5' end of the core sequence comprises a seed sequence consisting of any 6, 7, 8, 9 or 10 consecutive nucleotides of SEQ ID NO:6; or
   - (d) an external vector comprising a DNA sequence coding for the second microRNA; or
   - (e) two or more of (a)-(d).

2. The culture of claim 1, wherein the first microRNA comprises the nucleotide sequence of SEQ ID NO:2 or SEQ ID NO:1.

3. The culture of claim 1, wherein the second microRNA comprises the nucleotide sequence of SEQ ID NO:4 or of SEQ ID NO:3.

* * * * *